(12) United States Patent
Krueger et al.

(10) Patent No.: US 7,909,877 B2
(45) Date of Patent: Mar. 22, 2011

(54) SPINAL DISC IMPLANT WITH COMPLIMENTARY MEMBERS BETWEEN VERTEBRAL ENGAGING PLATES

(75) Inventors: David J. Krueger, Cedar Park, TX (US); Erik J. Wagner, Austin, TX (US)

(73) Assignee: Zimmer Spine, Inc., Minneapolis, MN (US)

(*) Notice: Subject to any disclaimer, the term of this patent is extended or adjusted under 35 U.S.C. 154(b) by 408 days.

(21) Appl. No.: 11/150,989

(22) Filed: Jun. 13, 2005

(65) Prior Publication Data
US 2006/0116768 A1 Jun. 1, 2006

Related U.S. Application Data

(63) Continuation of application No. 10/699,618, filed on Oct. 31, 2003, now abandoned.

(60) Provisional application No. 60/422,764, filed on Oct. 31, 2002.

(51) Int. Cl.
*A61F 2/44* (2006.01)

(52) U.S. Cl. ............ 623/17.15; 623/17.11; 623/17.14; 623/17.16

(58) Field of Classification Search ............ 606/61; 623/17.11–17.16
See application file for complete search history.

(56) References Cited

U.S. PATENT DOCUMENTS

| | | | | |
|---|---|---|---|---|
| 4,759,766 A | * | 7/1988 | Buettner-Janz et al. | 623/17.15 |
| 5,112,332 A | * | 5/1992 | Cozad et al. | 606/61 |
| 5,258,031 A | * | 11/1993 | Salib et al. | 623/17.15 |
| 5,314,477 A | * | 5/1994 | Marnay | 623/17.15 |
| 5,401,269 A | * | 3/1995 | Buttner-Janz et al. | 623/17.15 |
| 5,415,659 A | * | 5/1995 | Lee et al. | 606/61 |
| 5,425,773 A | * | 6/1995 | Boyd et al. | 623/17.15 |
| 5,534,029 A | * | 7/1996 | Shima | 623/17.15 |
| 5,888,226 A | * | 3/1999 | Rogozinski | 623/17.16 |
| 5,910,143 A | * | 6/1999 | Cripe et al. | 606/87 |
| 6,019,792 A | * | 2/2000 | Cauthen | 623/17.14 |

(Continued)

FOREIGN PATENT DOCUMENTS

AU 2003220366 B2 9/2003

(Continued)

OTHER PUBLICATIONS

Examiner Report issued in Australian Patent No. 2003287370 dated Mar. 26, 2008, Spinal Concepts, Inc., 3 pages.

(Continued)

*Primary Examiner* — Eduardo C Robert
*Assistant Examiner* — Julianna N Harvey
(74) *Attorney, Agent, or Firm* — Sprinkle IP Law Group

(57) ABSTRACT

Embodiments disclosed herein provide a disc implant for maintaining intervertebral spacing and stability within the human spine. In some embodiments, the disc implant includes complementary members between vertebral engaging plates. A first engaging plate may have a convex portion that allows anteroposterior translation of a first member relative to the first engaging plate. Movement of the first member relative to the first engaging plate allows lateral movement of vertebrae adjacent to the engaging plates. The first member may be coupled to a second member via complementary shapes such as a projection and a recess. The second member may have a convex portion that complements a recess of a second engaging plate. The recess may be concave with an arcuate cross-sectional shape in an anteroposterior plane. Movement of the second engaging plate relative to the second member allows for anteroposterior movement of vertebrae adjacent to the engaging plates.

20 Claims, 21 Drawing Sheets

U.S. PATENT DOCUMENTS

| | | | |
|---|---|---|---|
| 6,045,579 A * | 4/2000 | Hochshuler et al. | 623/17.16 |
| 6,146,421 A * | 11/2000 | Gordon et al. | 623/17.15 |
| 6,368,350 B1 | 4/2002 | Erickson et al. | |
| 6,936,071 B1 | 8/2005 | Marnay et al. | |
| 7,326,250 B2 * | 2/2008 | Beaurain et al. | 623/17.14 |
| 2002/0087212 A1 | 7/2002 | James et al. | |
| 2002/0183761 A1 * | 12/2002 | Johnson et al. | 606/90 |
| 2003/0187506 A1 * | 10/2003 | Ross et al. | 623/17.13 |
| 2003/0204261 A1 * | 10/2003 | Eisermann et al. | 623/17.14 |
| 2004/0002758 A1 | 1/2004 | Landry et al. | |
| 2004/0143332 A1 | 7/2004 | Krueger et al. | |
| 2004/0172135 A1 * | 9/2004 | Mitchell | 623/17.15 |
| 2006/0116768 A1 | 6/2006 | Krueger et al. | |

FOREIGN PATENT DOCUMENTS

| | | | |
|---|---|---|---|
| EP | 1374808 A1 | 1/2004 | |
| EP | 1567098 A2 | 8/2005 | |
| WO | WO 01/01893 A1 * | 1/2001 | |
| WO | WO0128463 A | 4/2001 | |
| WO | WO 01/62191 A | 8/2001 | |
| WO | WO 01/68003 A1 * | 9/2001 | |
| WO | WO 02/089701 A2 | 11/2002 | |
| WO | WO 03/077808 A3 | 9/2003 | |
| WO | WO 03/090648 A1 | 11/2003 | |
| WO | WO 2004/041131 A2 | 5/2004 | |

OTHER PUBLICATIONS

International Search Report mailed Jul. 9, 2004, in PCT/US0334641, Spinal Concepts, Inc., 11 pages Office Action issued in U.S. Appl. No. 10/699,618, dated Dec. 13, 2004, David J. Krueger, 5 pages.

European Search Report issued in Patent Application No. EP 03781603, dated Oct. 17, 2007, Spinal Concepts, Inc., 2 pages.

Office Action issued in Patent Application No. EP 03781603.0 mailed Jan. 22, 2008, Spinal Concepts, Inc., 2 pages.

Examiner Report issued in Australian Patent Application No. 200328370 dated Nov. 19, 2008, 3 pages.

Office Action issued in Patent Application No. EP 03781603.0 mailed Feb. 16, 2009, Spinal Concepts, Inc., 5 pages.

Examination Report for European Patent Application No. 03781603.0, issued on Jan. 22, 2010, 5 pgs.

Canadian Office Action for Application No. 2,502,292, issued on Feb. 23, 2010, 2 pgs.

Office Action issued in Japanese Patent Application No. 2004-550317, mailed Sep. 15, 2009, 4 pgs (translated copy).

Canadian Office Action for Canadian Application No. 2,502,292, issued on Aug. 13, 2010, 2 pgs.

* cited by examiner

SPINAL DISC IMPLANT WITH COMPLIMENTARY MEMBERS BETWEEN VERTEBRAL ENGAGING PLATES

PRIORITY CLAIM

The present application is a continuation of U.S. patent application Ser. No. 10/699,618, entitled "MOVABLE DISC IMPLANT," filed on Oct. 31, 2003 now abandoned, which claims priority to U.S. Provisional Patent Application No. 60/422,764, entitled "MOVABLE DISC IMPLANT," filed on Oct. 31, 2002. The above-referenced applications are hereby incorporated in their entirety by reference as if fully set forth herein.

BACKGROUND

1. Field of Invention

The present invention generally relates to the field of medical devices. Some embodiments of the invention relate to spinal disc implants and instruments used to insert the implants. Other embodiments of the invention relate to methods of forming spinal disc implants and methods for positioning the implants during surgical procedures.

2. Description of Related Art

Bone may be subject to degeneration caused by trauma, disease and/or aging. Degeneration may destabilize bone and affect surrounding structures. For example, destabilization of a spine may result in alteration of a natural spacing between adjacent vertebrae. Alteration of a natural spacing between adjacent vertebrae may subject nerves that pass between vertebral bodies to pressure. Pressure applied to the nerves may cause pain and/or nerve damage. Maintaining the natural spacing between vertebrae may reduce pressure applied to nerves that pass between vertebral bodies. A disc implant may be used to maintain the natural spacing between vertebrae and to inhibit relative motion of the vertebrae.

A disc space may be created by full or partial removal of an intervertebral disc between two vertebral bodies. Spinal implants for a lumbar region of the spine may be positioned in an intervertebral space after a discectomy procedure. The implant may be inserted using an anterior, lateral and/or posterior approach. The spinal implant may be a fusion device or an artificial disc. Conventional systems and methods for posterolateral spinal fusion may involve dissecting and retracting soft tissue proximate the surgical site. Dissection and retraction of soft tissue may cause trauma to the soft tissue and extend recovery time. Minimally invasive procedures and systems may reduce recovery time as well as trauma to the soft tissue surrounding a stabilization site.

Spinal disc implants and/or disc implant insertion instruments are described in U.S. Pat. No. 5,676,701 to Yuan et al.; U.S. Pat. No. 5,401,269 to Buttner-Janz et al.; U.S. Pat. No. 5,370,697 to Baumgartner; U.S. Pat. No. 5,314,477 to Marnay and International Application No. WO 01/19295 to Marnay, all of which are incorporated by reference as if fully set forth herein.

SUMMARY

In certain embodiments, a disc implant may be used to stabilize vertebrae of a human spine while allowing normal movement of the vertebrae relative to each other. An artificial disc implant may replace a diseased or defective intervertebral disc. An artificial disc implant may be easy to install with only minimal intrusion to adjacent tissue and muscle. A disc implant may introduce minimal risk of dural damage or neural damage during installation and use.

An artificial disc implant may include one or more engaging plates and one or more members. Engaging plates may fit between and engage adjacent vertebrae of the spine. The plates may maintain a space between the adjacent vertebrae. One or more members may be positioned in the space between the engaging plates. Engaging plates and members may be designed to allow axial rotation, anteroposterior movement and/or lateral movement of adjacent vertebrae (i.e., the spine). Lateral movement may include lateral bending. Anteroposterior movement may include flexion and/or extension. In some embodiments, a range of motion of one engaging plate relative to another engaging plate may be limited.

In some embodiments, an engaging plate may include a recess complementary to a portion of a member. In certain embodiments, an engaging plate may include slots. The slots may be dovetailed. The slots may be complementary to a portion of an instrument used to insert engaging plates between vertebrae. In some embodiments, slots may be formed at an angle relative to an anterior-posterior axis of an engaging plate. In some embodiments, an angular orientation of a recess may correspond to an angle of slots in an engaging plate. Angulation of the slots may allow insertion of a disc implant using a modified (e.g., angulated) anterior approach. A modified anterior approach may facilitate retraction of blood vessels above the L5 vertebrae.

In certain embodiments, an engaging plate may include one or more coupling projections. One or more coupling projections may penetrate a vertebral surface. In some embodiments, a coupling projection may be positioned in a recess formed in a vertebral surface. Once positioned in the vertebra, the coupling projection may inhibit movement of an engaging plate relative to the vertebra.

In some embodiments, a disc implant may include two engaging, plates and a member. The member may have a convex portion. The engaging plates may be shaped to complement surfaces of the member, including the convex portion. The member may be positioned between the engaging plates to allow axial rotation, lateral and/or anteroposterior movement of a first engaging plate relative to a second engaging plate.

In disc implant embodiments including two engaging plates and a member, the member may allow the engaging plates to undergo three independent components of motion relative to each other. The member may have a convex portion and a recess. The recess of the member may complement a projection on a first engaging, plate to allow rotation of a first engaging plate relative to the member. The convex portion of the member may complement a concave portion of the second engaging plate to allow anteroposterior and/or lateral movement of the second engaging plate relative to the member.

In some embodiments, a disc implant may include two engaging plates and two members. The members may allow the engaging plates to undergo three independent components of motion relative to each other. A convex portion of a first engaging plate may complement a concave portion of a first member to allow lateral bending of the first engaging plate relative to a second engaging plate. A projection on the first member may complement a recess in a second member to allow axial rotation of the first engaging plate relative to the second engaging plate. A convex portion of the second member may complement a concave portion of the second engaging plate to allow movement of the engaging plates relative to each other.

In other disc implant embodiments including two engaging plates and two members, a first member may couple to a first engaging plate to allow axial rotation of the first engaging plate relative to a second engaging plate. A convex portion of the first member may complement a concave portion of a second member to allow lateral bending of the engaging plates relative to each other. A convex portion of the second member may complement a concave portion of the second engaging plate to allow flexion and/or extension of vertebrae adjacent to the engaging plates.

In disc implant embodiments including a member and two engaging plates, a member may have a spherical shape. The member may be positioned between concave portions of the engaging plates. The member may allow axial rotation, anteroposterior movement and/or lateral movement of the engaging plates relative to each other.

An instrumentation set for a disc implant insertion procedure may include various guidance and/or insertion instruments. Insertion instruments may include, but are not limited to, chisels, reamers, hex drivers, slap hammers, inserters, distractors and pushers. An instrumentation set may include trial endplates and disc implant components. Trial endplates may be plates of various sizes and lordotic alignment. Trial endplates may include stops and/or instrument guides to facilitate removal of bone material from a vertebral surface. Distractors in combination with trial endplates may determine a size, height and lordotic alignment of implant components to be used in a disc implant insertion procedure. Implant components may include, but are not limited to, engaging plates of various sizes and lordotic alignment and members of various sizes and shapes.

An inserter may be used to position engaging plates between two vertebrae. A distractor may be positioned between the engaging plates to establish a desired separation distance between the engaging plates. One or more members may be guided through a body of the distractor and into the space between the engaging plates. In some embodiments, members may be guided through a body of a distractor with a pusher. The pusher may maintain the position of the members when a distractor is removed from the inserter.

In certain embodiments, trial endplates, members and engaging plates may be formed from various materials including plastics, ceramics, polymers, composites and metals. Materials may be chosen based on factors including, but not limited to, durability, biocompatibility, galling characteristics, mechanical strength and/or wear properties. In some embodiments, radiological markers may be used in combination with materials that are "invisible" to radiological techniques. In certain embodiments, steps may be taken to adjust a coefficient of friction of materials chosen to form members (e.g., surfaces may be polished or roughened). In other embodiments, surfaces of engaging plates and/or members may be coated to reduce noise created by contact of a member with an engaging plate and/or another member.

BRIEF DESCRIPTION OF THE DRAWINGS

Advantages of the present invention will become apparent to those skilled in the art with the benefit of the following detailed description and upon reference to the accompanying drawings in which.

Figure 1:
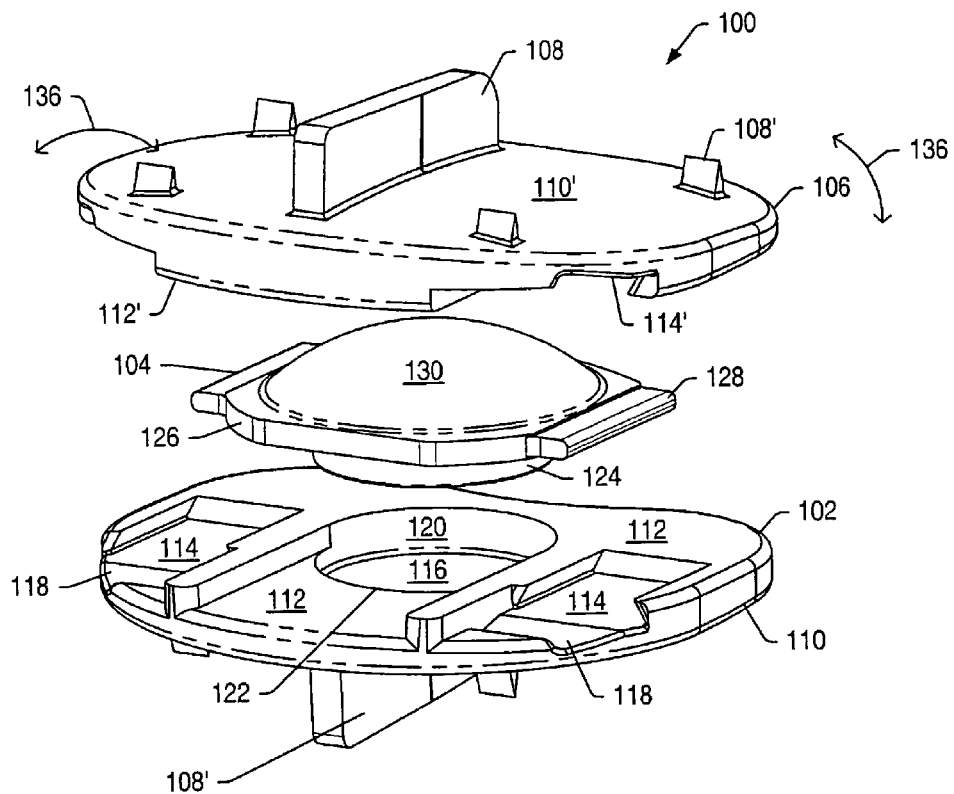
FIG. 1 is a perspective view of components of a disc implant.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION

An intervertebral disc implant may be used to stabilize a portion of the spine. The artificial intervertebral disc implant may replace all or a portion of an intervertebral disc that requires replacement due to degeneration from natural wear, trauma or disease. The artificial intervertebral disc may restore the normal separation distance between the vertebrae and allow normal movement and flexibility of the spine.

Disc implants may allow movement of adjacent vertebrae relative to each other in ranges associated with normal limits for human vertebrae. Disc implants may allow axial rotation, axial compression and lateral and/or anteroposterior movement. In a human spine, axial rotation may include rotation of about 0.1° to about 3° about a longitudinal axis of the spine. An axis of rotation between vertebrae may be off-center due to the fibrocartilaginous nature of an intervertebral disc. An axis of rotation between two vertebrae may be located posterior to a mid-point between the vertebrae. Lateral movement may include lateral bending. Lateral bending may include motion to the left and/or right up to a maximum of about 0.5° to about 10°. Anteroposterior movement may include flexion and/or extension. Flexion may include anterior motion up to a maximum of about 0.5° to about 20°. Extension may include posterior motion up to a maximum of about 0.5° to about 10°.

Some implant embodiments may inhibit movement outside of normal limits for vertebrae. Limiting a range of motion may decrease chances of injury. Tissue and structure adjacent to vertebrae separated by a disc may limit some ranges of motion. For example, surrounding tissue and structure may limit axial rotation of vertebrae.

In some embodiments, artificial disc implants may be used to replace a disc or discs in the lumbar region of a spine. In certain embodiments, artificial disc implants may be used in cervical or thoracic portions of the spine. In some embodiments, artificial disc implants may be used with other systems or devices to provide stability to the spine. In other embodiments, a disc implant may be used as a stand-alone system.

FIG. 1 is a perspective view of components of an embodiment of a disc implant that may be inserted between two vertebrae. Disc implant 100 may include engaging plate 102, member 104 and engaging plate 106. When the implant is installed in a patient, each engaging plate of the implant may cover at least 70% of the vertebral surface that the engaging plate contacts. Member 104 may separate engaging plate 102 from engaging plate 106. In certain embodiments, member 104 may be held between engaging plates 102, 106 at least partially by pressure resulting from natural compression of the spine.

Engaging plates 102, 106 may contact adjacent vertebrae to anchor the disc implant to the spine. Coupling projections 108 positioned on outer surfaces 110, 110' of engaging plates 102, 106 may be positioned in a recess of a vertebral surface. Coupling projections 108' positioned on outer surfaces 110, 110' of engaging plates 102, 106 may penetrate into vertebral surfaces to inhibit movement of the engaging plates relative to the vertebrae. In certain embodiments, engaging plates may be coupled to vertebrae using methods other than, or in addition to, coupling projections 108, 108'. For example, fasteners may be used to attach an engaging plate to a vertebra. Fasteners may include, but are not limited to, screws, nails, rivets, trocars, pins and barbs.

Inner surface 112 of engaging plate 102 may include slots 114 and recess 116. Slots 114 may have a cross-sectional shape including, but not limited to, square, rectangular, trapezoidal, or irregular. Inner surface 112' of engaging plate 106 may include slots 114' that align with slots 114 of engaging plate 102 when disc implant 100 is assembled. Slots 114, 114' may include indents 118. Indents 118 may engage an instrument used to facilitate insertion of implant 100 during a surgical procedure. In some embodiments, slots 114, 114' may be dovetailed. Slots 114, 114' may allow use of insertion instruments without adding a height and/or a thickness to the overall dimension of implant 100.

Figure 2:
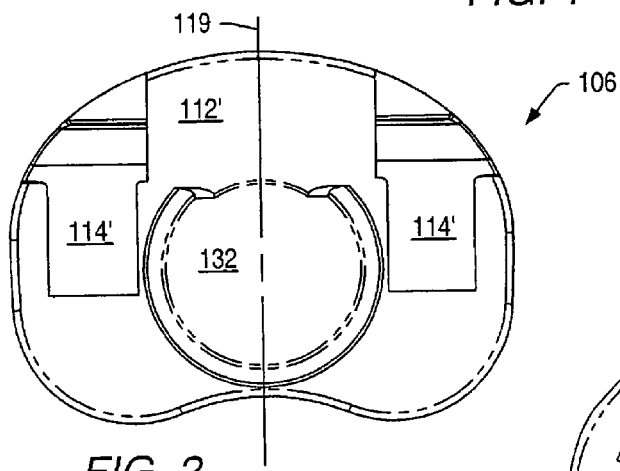
FIG. 2 is a bottom view of an embodiment of an engaging plate.
Figure 3:
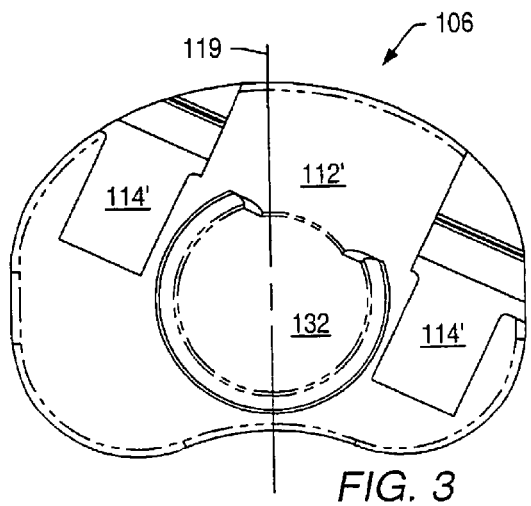
FIG. 3 is a bottom view of an embodiment of an engaging plate.

In some embodiments, slots in an engaging plate may be parallel or substantially parallel to an anterior-posterior axis of the engaging plates. FIG. 2 depicts an embodiment of engaging plate 106 wherein slots 114' are parallel to anterior-posterior axis 119. In some embodiments, slots may be at acute angle relative to the anterior-posterior axis of the engaging plate. FIG. 3 depicts an embodiment of engaging plate 106 wherein slots 114' are angled relative to anterior-posterior axis 119. Slots 114, 114' may be formed at an angle ranging from about 15° to about 30° relative to anterior-posterior axis 119. In some embodiments, slots 114, 114' may be formed at about a 25° angle relative to anterior-posterior axis 119. Angulation of slots 114, 114' may allow insertion of implant 100 using a modified (e.g., angulated) anterior approach. In some embodiments, an angular orientation of recess 116 may correspond to angulation of slots 114, 114'. A modified anterior approach may facilitate retraction of blood vessels above the L5 vertebrae. In some embodiments, engaging plates 102, 106 with slots 114, 114' angled relative to anterior-posterior axis 119 may not include a central coupling projection (i.e., a keel).

Recess 116 of engaging plate 102 may have a cross-sectional shape including, but not limited to, circular, elliptical, square, rectangular or irregular. Sides of recess 116 may be tapered. Posterior side 120 of recess 116 may be at least twice the height of anterior side 122 of recess 116. A height difference between anterior side 122 and posterior side 120 may minimize overdistraction of the vertebrae required during positioning of member 104 between engaging plates 102, 106 in a disc implant procedure. In some embodiments, a bottom portion of the recess may include an opening or openings to allow residual body fluids and/or bone matter to be removed from the recess.

Base 124 of member 104 may fit in recess 116 of engaging plate 102. Base 124 may substantially conform to the shape of recess 116. In some embodiments, member 104 may be a tapered boss. A width of base 124 that fits in recess 116 may be slightly less than a width of the recess to allow member 104 to translate in the recess. Recess 116 may maintain a position of member 104 between engaging plates 102, 106.

Member 104 may include center section 126. A height of center section 126 of member 104 may add thickness to a height of implant 100. Center section 126 may range in height from about 5 mm to about 20 mm. In certain embodiments, center section 126 may have a height of about 9 mm. In some embodiments, center section 126 may have a height of about 11 mm. In other embodiments, center section 126 may have a height of about 13 mm.

Center section 126 may include projections 128. Projections 128 may be an integral part of center section 126. In some embodiments, projections 128 may be glued, press fit and/or welded to center section 126. Projections 128 may be the same height as center section 126. Projections 128 may engage an instrument to facilitate insertion of member 104 between engaging plates 102, 106.

Member 104 may include convex portion 130. Convex portion 130 may be, but is not limited to being, an ellipsoidal section, an ovate section or a spherical section. Inner surface 112' of engaging plate 106 may include a recess. FIG. 2 depicts a bottom view of inner surface 112' of engaging plate 106 shown in FIG. 1. Recess 132 may complement convex portion 130 of member 104. In some embodiments, a height of convex portion 130 may exceed a depth of recess 132. As used herein, "complement" or "complementary" refers to shapes of implant components that fit together to allow smooth relative motion of the components.

FIG. 3 depicts a bottom view of inner surface 112' of an embodiment of engaging plate 106 with slots 114' angled relative to anterior-posterior axis 119. Slots 114' may be formed at an angle ranging from about 15° to about 30° relative to anterior-posterior axis 119. In some embodiments, slots 114' may be formed at about a 25° angle relative to anterior-posterior axis 119. In certain embodiments, an orientation of recess 132 may be angled to correspond to an angle of slots 114'. Angulation of slots 114' may allow insertion of implant 100 using a modified (e.g., angulated) anterior approach.

Figure 4:
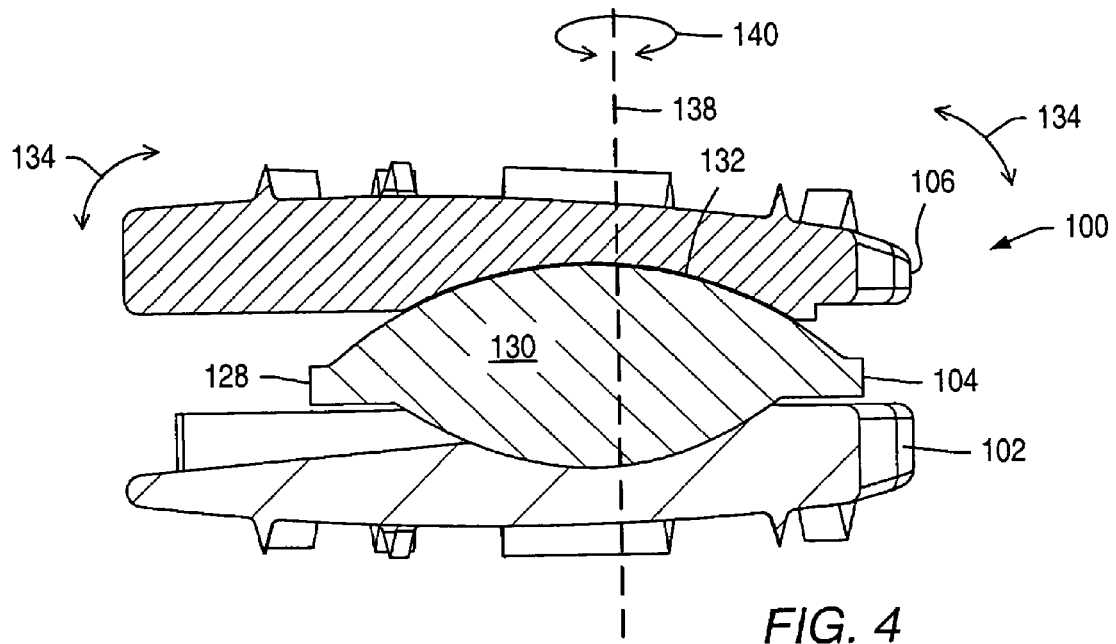
FIG. 4 is a cross-sectional view of an embodiment of a disc implant.

FIG. 4 depicts a cross-sectional view of the implant shown in FIG. 1 after the implant has been assembled. Convex portion 130 of member 104 may complement recess 132 of engaging plate 106. A shape of convex portion 130 may allow engaging plate 106 to move (e.g., rock) in an anteroposterior plane and/or a mediolateral plane relative to engaging plate 102. Movement of engaging plate 106 relative to engaging plate 102 in the anteroposterior plane indicated by arrow 134 may allow flexion and extension of vertebrae adjacent to the engaging plates. Movement of engaging plate 106 relative to engaging plate 102 in the mediolateral plane indicated by arrow 136 in FIG. 1 may allow lateral bending of the vertebrae adjacent to engaging plates 102, 106. Engaging plate 106 may rotate relative to engaging plate 102 around axis of rotation 138 in the plane indicated by arrow 140. In some embodiments, axial rotation of engaging plate 106 relative to engaging plate 102 may be limited by tissue, bone or other material in the patient.

In some embodiments, a height of convex portion 130 and a depth of recess 132 may be chosen to limit lateral movement of engaging plate 106 relative to engaging plate 102. For example, a height of convex portion 130 may allow engaging plate 106 to contact engaging plate 102 when engaging plate 106 rocks in the direction of engaging plate 102. Contact of inner surfaces 112, 112' of engaging plates 102, 106 may provide a limit to anteroposterior movement of engaging plate 106 relative to engaging plate 102. Contact of inner surfaces 112, 112' of engaging plates 102, 106 may limit flexion and/or extension of the adjacent vertebrae. A height of convex portion 130 may determine maximum flexion and/or extension allowed by the implant. In some embodiments, a maximum amount of flexion may be limited to a range between about 0.5° and about 20°. In some embodiments, maximum flexion allowed by the implant may be about 10°. In other embodiments, maximum flexion allowed by the implant may be about 15°. In some embodiments, a maximum amount of extension may be limited to a range between about 0.5° and about 12°. In some embodiments, maximum extension allowed by the implant may be about 8°. In other embodiments, maximum extension allowed by the implant may be about 5°.

In some embodiments, components of an implant may include surfaces that contact to limit a maximum amount of lateral bending. In some embodiments, an implant may allow equal amounts of lateral bending so that the patient can laterally bend the same amount to the right or the left. In some embodiments, a maximum amount of lateral bending to the left may be different than a maximum amount of lateral bending to the right to accommodate specific needs of a patient. In some embodiments, an implant may be designed to allow a maximum amount of lateral bending within a range between ±0.5° to about ±15°. In some embodiments, the maximum amount of lateral bending may be about ±10°. In some embodiments, the maximum amount of lateral bending allowable by an implant may be about ±5°.

Figure 5:
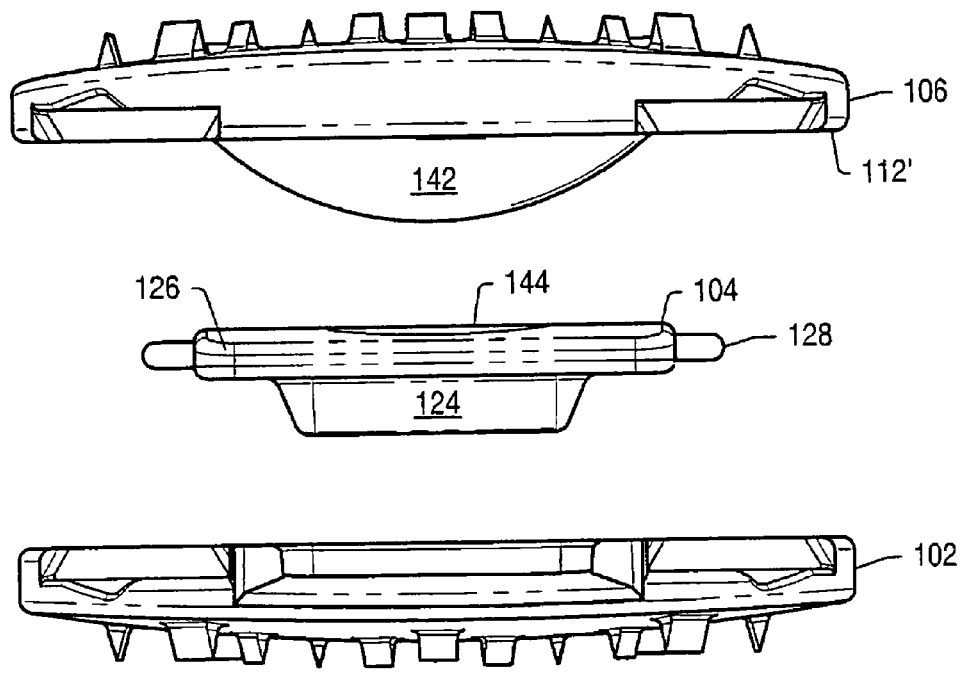
FIG. 5 is a side view of components of a disc implant.

In alternative embodiments, a concave portion of a member may complement a convex portion of an engaging plate. As shown in FIG. 5, convex portion 142 of engaging plate 106 may complement recess 144 of member 104 to form an implant. A large contact area between engaging plate 106 and member 104 may advantageously distribute a compressive load applied to the implant over a relatively large area.

Figure 6:
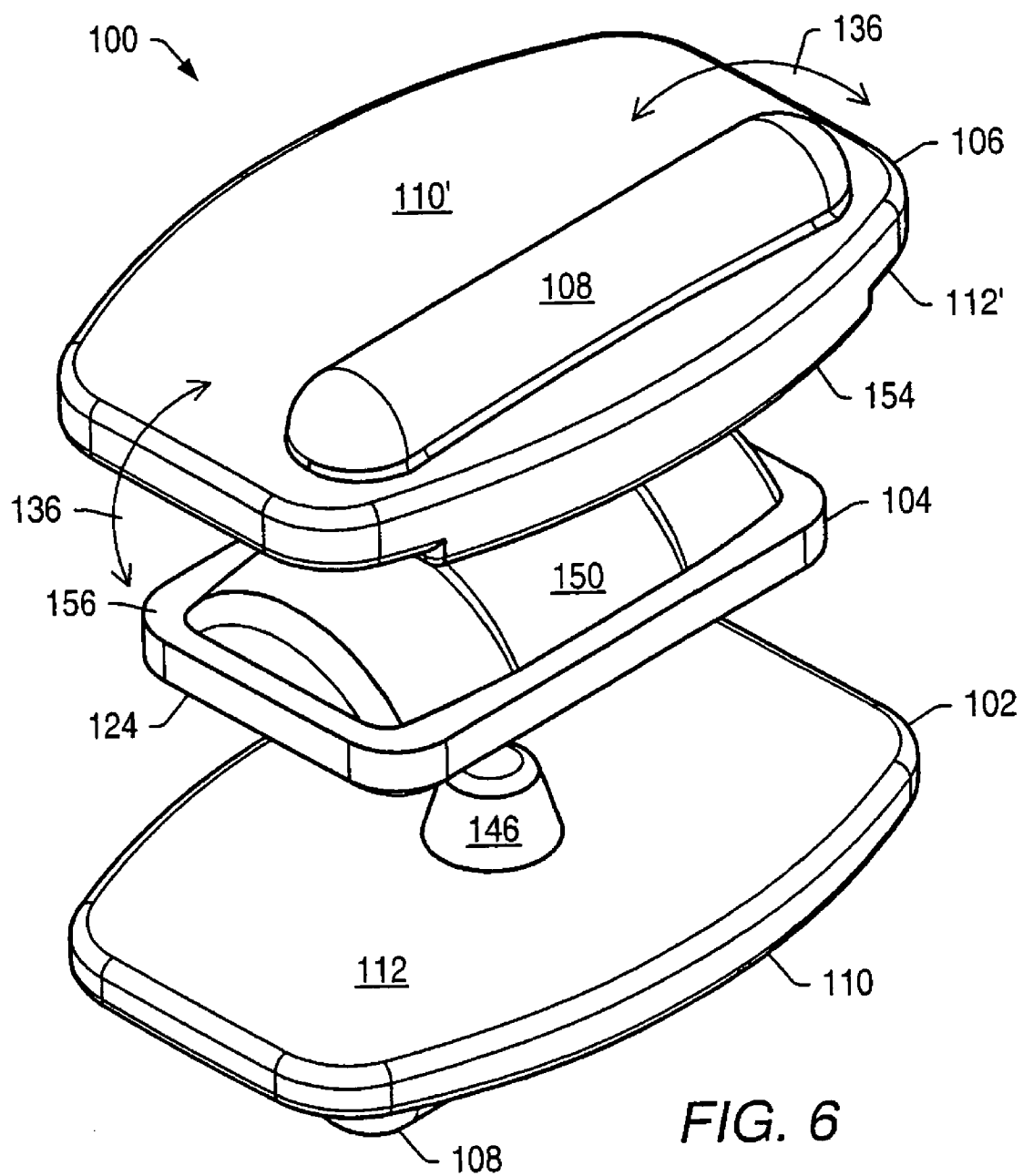
FIG. 6 is a perspective view of components of a disc implant.

FIG. 6 depicts a perspective view of components of an implant embodiment. Implant 100 may allow a full range of physiological movement of vertebrae adjacent to the implant. Inner surface 112 of engaging plate 102 may include at least one projection. Projection 146 may be coupled to engaging plate 102. In some embodiments, projection 146 may be an integral part of engaging plate 102. Projection 146 may have a shape that allows engaging plate 102 to rotate freely relative to member 104. The shape of projection 146 may be, but is not limited to being, tapered, round or square. Member 104 may include recess 148 (shown in FIG. 7). Recess 148 may complement projection 146. Recess 148 may have a slightly larger cross section than projection 146 to allow engaging plate 102 to move relative to member 104. A size and/or shape of recess 148 relative to projection 146 may determine a range of rotation of member 104 relative to engaging plate 102.

Figure 7:
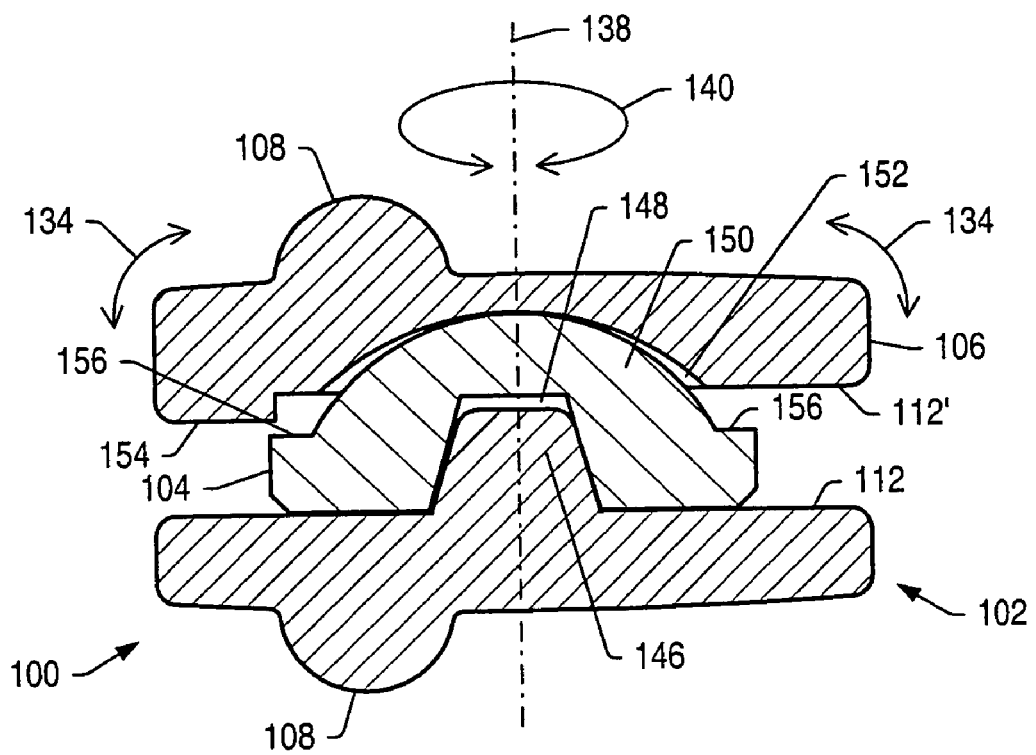
FIG. 7 is a cross-sectional view of an embodiment of a disc implant.

As depicted in FIG. 7, recess 148 and projection 146 may define axis of rotation 138. Friction between engaging plate 102 and member 104 may be low enough to allow rotation of the engaging plate relative to the member. Engaging plate 102 may rotate relative to member 104 as indicated by arrow 140. Rotation of engaging plate 102 relative to member 104 may imitate axial rotation of the spine. A large contact area between recess 148 of member 104 and projection 146 of engaging plate 102 may distribute a compressive load applied to implant 100 over a relatively large surface area.

Member 104 may include convex portion 150. Inner surface 112' of engaging plate 106 may include recess 152. Recess 152 of engaging plate 106 may complement convex portion 150 of member 104. The shape of convex portion 150 may allow engaging plate 106 to move (e.g., rock) relative to member 104. Movement of engaging plate 106 relative to member 104 may allow lateral movement (e.g., lateral bending) of vertebrae adjacent to the engaging plates. In an alternative embodiment, member 104 may include a recess complementary to a convex part of engaging plate 106.

Convex portion 150 may have an arcuate cross-sectional shape in an anteroposterior plane and/or in a mediolateral plane. An arcuate shape of convex portion 150 in the anteroposterior plane may allow engaging plate 106 to rock relative to engaging plate 102 in the directions indicated by arrows 134 in FIG. 7. Movement of engaging plate 106 relative to engaging plate 102 in the anteroposterior plane may allow flexion and extension of vertebrae adjacent to the engaging plates. An arcuate shape of convex portion 150 in the mediolateral plane may allow engaging plate 106 to move relative to engaging plate 102 in directions indicated by arrow 136 in FIG. 6. Movement of engaging plate 106 relative to engaging plate 102 in the mediolateral plane may allow lateral bending of vertebrae adjacent to the engaging plates.

Figure 8:
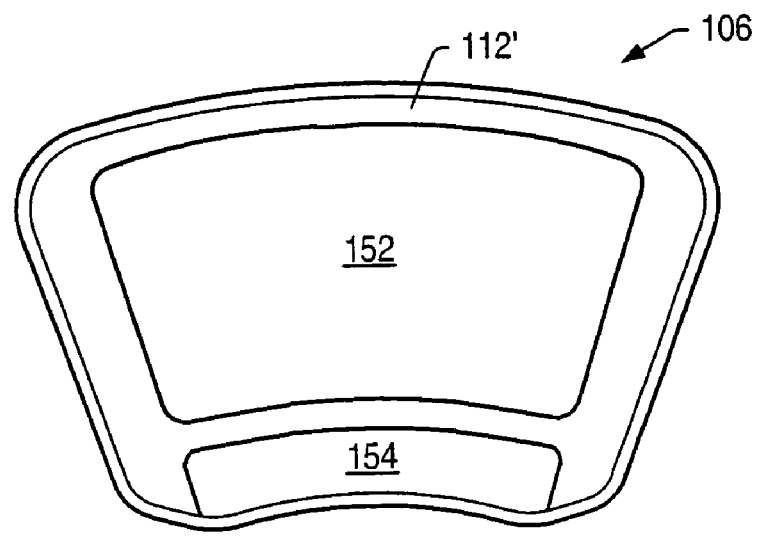
FIG. 8 is a bottom view of an engaging plate.

FIG. 8 depicts a bottom view of inner surface 112' of engaging plate 106 shown in FIG. 7. Engaging plate 106 may include recess 152. A shape of recess 152 may complement convex portion 150 of member 104. Recess 152 may be concave with an arcuate cross-sectional shape in an anteroposterior plane and/or in a mediolateral plane. A shape of recess 152 may allow movement of engaging plate 106 relative to member 104 in an anteroposterior plane and/or in a mediolateral plane. Movement of engaging plate 106 relative to member 104 in an anteroposterior plane and/or in a mediolateral plane may allow flexion, extension and/or lateral bending of vertebrae adjacent to engaging plates 102, 106.

In some embodiments, engaging plate 106 may include limiter 154, as shown in FIG. 7. Limiter 154 may be positioned to contact surface 156 of member 104. Contact of limiter 154 and surface 156 may limit posterior movement of engaging plate 106 relative to engaging plate 102. Contact of limiter 154 and surface 156 may therefore limit extension of vertebrae adjacent to engaging plates 102, 106. A height of limiter 154 relative to inner surface 112' of engaging plate 106 and/or a height of surface 156 relative to inner surface 112 of engaging plate 102 may be chosen to limit extension of vertebrae adjacent the implant. Maximum extension allowed by implant 100 may range from about 3° to about 12°. In some embodiments, maximum extension allowed by implant 100 may be about 8°. In other embodiments, maximum extension allowed by implant 100 may be about 5°.

In some embodiments, inner surface 112' of engaging plate 106 may contact surface 156 of member 104. Contact of inner surface 112' with surface 156 may limit anterior movement of engaging plate 106 relative to engaging plate 102. Contact of inner surface 112' of engaging plate 106 with surface 156 of member 104 may limit flexion of vertebrae adjacent engaging plates 102, 106. A height of surface 156 relative to inner surface 112 of engaging plate 102 may be chosen to limit flexion of vertebrae adjacent to engaging plates 102, 106. Maximum flexion allowed by implant 100 may range from about 5° to about 20°. In some embodiments, maximum flexion allowed by implant 100 may be about 10°. In other embodiments, maximum flexion allowed by implant 100 may be about 15°.

Figure 9:
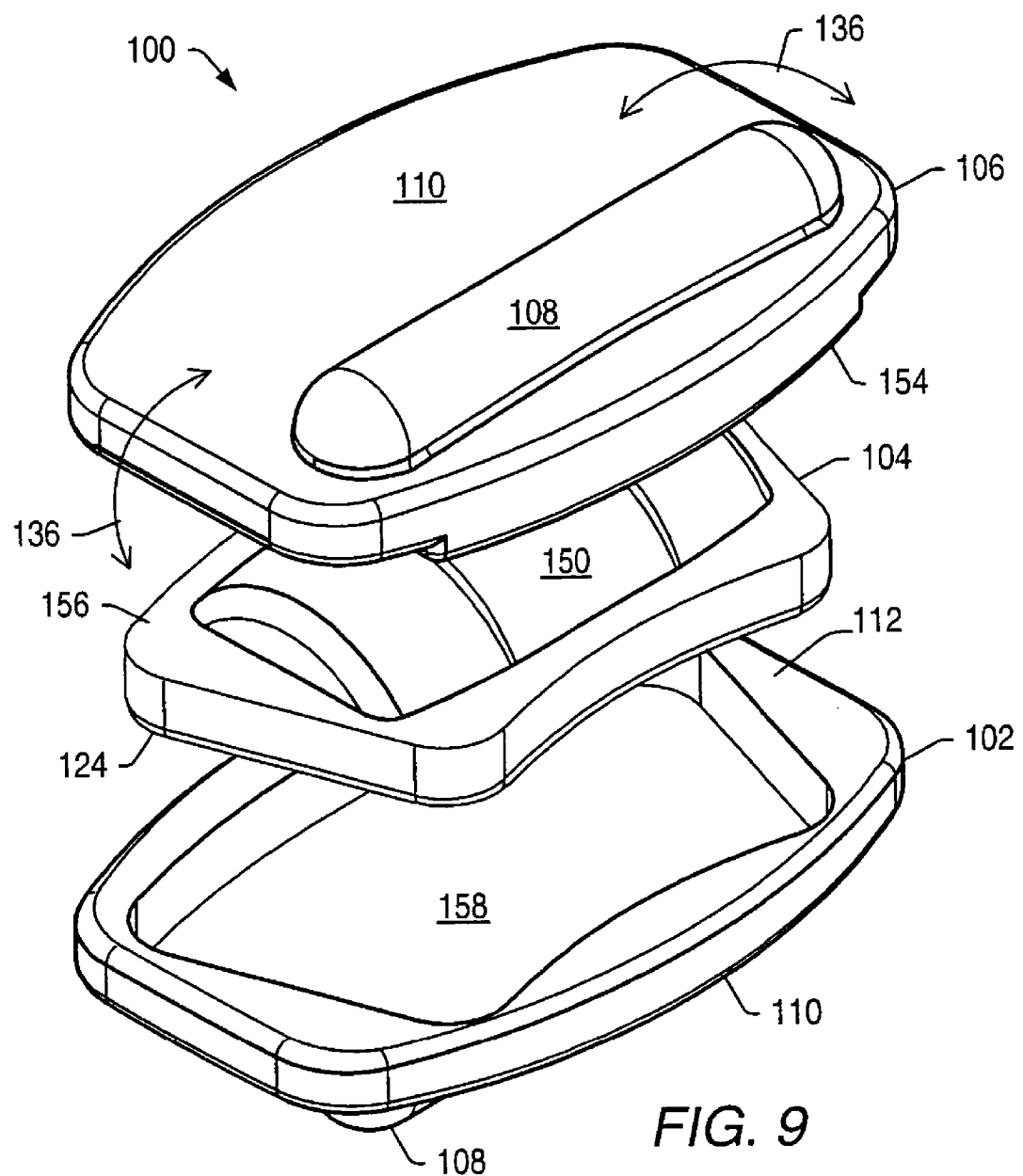
FIG. 9 is a perspective view of components of a disc implant.

FIG. 9 depicts a perspective view of components of an embodiment of an implant. Implant 100 may allow limited axial rotation of vertebrae adjacent to engaging plates 102, 106. Engaging plate 102 may include recess 158. Edges of recess 158 may be arced. The arcs may share a common center point. Base 124 of member 104 may fit in recess 158. A surface of base 124 may substantially conform to an arced surface of recess 158. A width of base 124 may be less than a width of recess 158 such that member 104 may be able to translate in recess 158 along curves defined by the edges of the recess.

Figure 10:
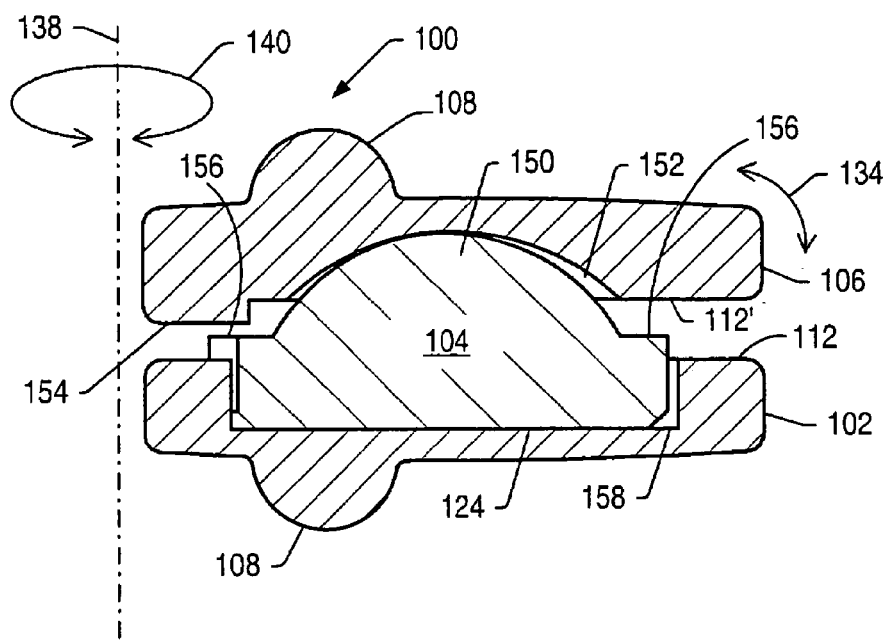
FIG. 10 is a cross-sectional view of an embodiment of a disc implant.

FIG. 10 depicts a cross-sectional view of the implant shown in FIG. 9 after the implant has been assembled. Base 124 of member 104 may complement recess 158 of engaging plate 102. Axis of rotation 138 may be at or near the centroid of engaging plates 102, 106 or offset from the engaging plates. Rotation of engaging plate 102 relative to engaging plate 106 may allow rotation of vertebrae adjacent implant 100.

A shape of recess 158 may allow engaging plate 102 to rotate axially relative to engaging plate 106 in the plane indicated by arrow 140. Movement of base 124 in recess 158 may limit axial rotation of the vertebrae adjacent to engaging plates 102, 106. Maximum axial rotation allowed by implant 100 may range from about ±0.1° to about ±6°. In some embodiments, maximum axial rotation allowed by implant 100 may be about ±3°. In other embodiments, maximum axial rotation allowed by implant 100 may be about ±1°.

Engaging plate 106 may include recess 152. Recess 152 may complement convex portion 150 of member 104. In an alternative embodiment, member 104 may include a recess complementary to a convex portion of engaging plate 106. Convex portion 150 may have an arcuate cross-sectional shape in an anteroposterior plane and/or in a mediolateral plane. An arcuate shape of convex portion 150 in an anteroposterior plane may allow engaging plate 106 to move (e.g., rock) relative to member 104 in the directions indicated by arrow 134. Movement of engaging plate 106 relative to member 104 in the anteroposterior plane may allow flexion and/or extension of the vertebrae adjacent to the engaging plates. An arcuate shape of convex portion 150 in a mediolateral plane may allow engaging plate 106 to move (e.g., rock) relative to member 104 in the directions indicated by arrows 136 in FIG. 9. Movement of engaging plate 106 relative to member 104 in the mediolateral plane may allow lateral bending of the vertebrae adjacent to the engaging plates.

In some embodiments, inner surface 112' of engaging plate 106 (shown in FIG. 10) may contact surface 156 of member 104. Contact of inner surface 112' with surface 156 may limit movement of engaging plate 106 relative to engaging plate 102 in the anteroposterior plane. Contact of inner surface 112' with surface 156 may limit flexion of the spine. In certain embodiments, a height of a surface 156 relative to inner surface 112 may be chosen to limit flexion of the spine. Maximum flexion allowed by implant 100 may range from about 5° to about 20°. In some embodiments, maximum flexion allowed by implant 100 may be about 10°. In other embodiments, maximum flexion allowed by implant 100 may be about 15°.

In some embodiments, posterior movement of engaging plate 106 relative to engaging plate 102 may be limited. Engaging plate 106 may include limiter 154. During use, limiter 154 may contact surface 156 to limit posterior movement of engaging plate 106 relative to engaging plate 102. Contact of limiter 154 with surface 156 may limit extension of the spine. A height of limiter 154 relative to inner surface 112' and/or a height of contact surface 156 relative to inner surface 112 may be chosen to limit extension of the spine. Maximum extension allowed by implant 100 may range from about 3° to about 12°. In some embodiments, maximum extension allowed by implant 100 may be about 8°. In other embodiments, maximum extension allowed by implant 100 may be about 5°.

In some embodiments, inner surface 112 of engaging plate 102 may have a convex portion. Engaging plate 102 of implant 100 shown in FIG. 11 includes convex portion 160. Convex portion 160 may have an arcuate cross-sectional shape in an anteroposterior plane and/or in a mediolateral plane. Member 104 may include recess 162, as shown in FIG. 12. Edges of recess 162 may be arced. The arcs may share a common center point. Convex portion 160 may fit in recess 162 of member 104. Convex portion 160 of engaging plate 102 may complement recess 162. A width of convex portion 160 may be less than a width of recess 162. Engaging plate 102 may translate in recess 162 along curves defined by edges of the recess.

Figure 11:
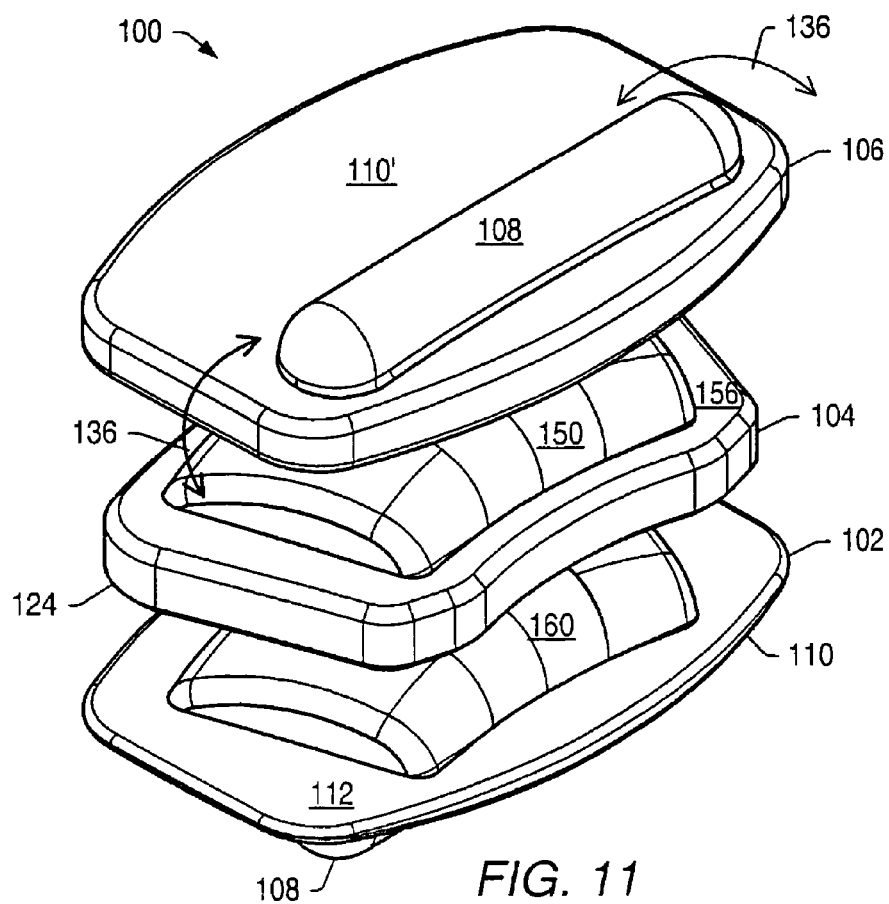
FIG. 11 is a perspective view of components of a disc implant.
Figure 12:
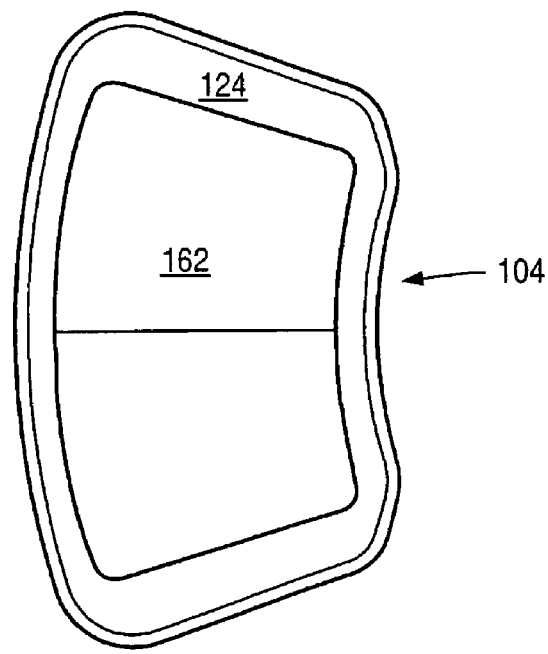
FIG. 12 is a top view of a member.
Figure 13:
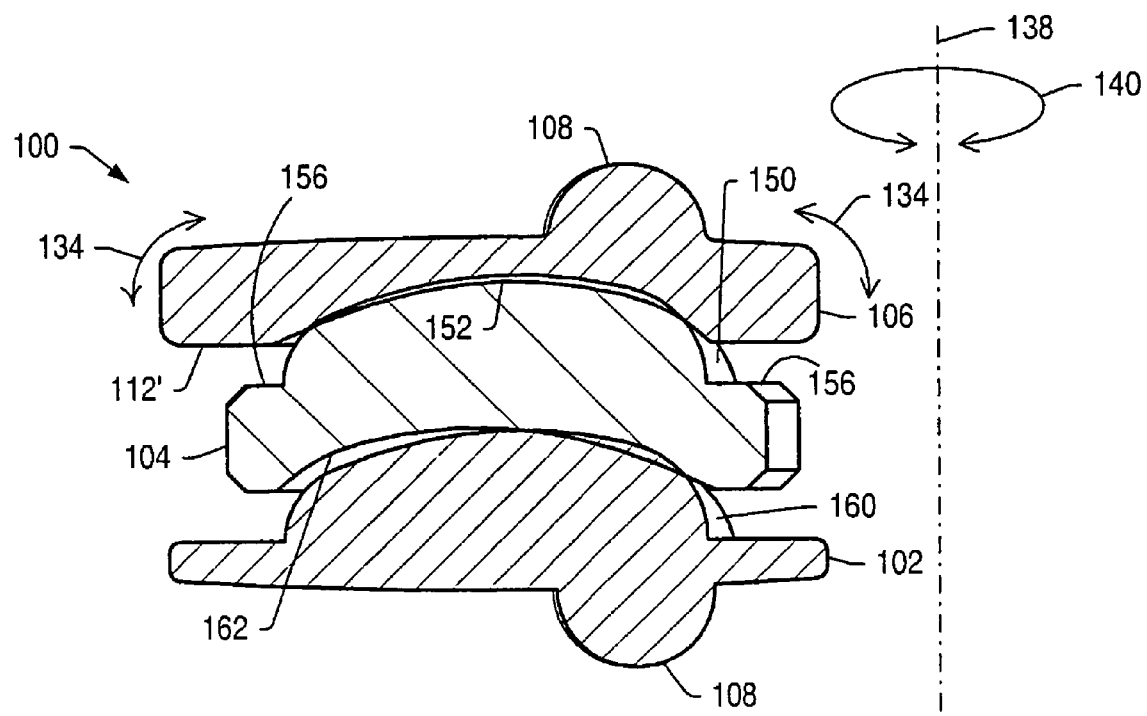
FIG. 13 is a cross-sectional view of an embodiment of a disc implant.

FIG. 13 depicts a cross-sectional view of the implant shown in FIG. 11 after the implant has been assembled.

Recess 162 of member 104 may complement convex portion 160 of engaging plate 102. A shape of convex portion 160 may allow relative movement of engaging plates 102, 106 in the plane indicated by arrow 140 about axis of rotation 138. Axis of rotation 138 may be at or near the centroid of implant 100 or offset from the centroid.

Maximum axial rotation allowed by implant 100 may range from about ±0.1° to about ±6°. In some embodiments, maximum axial rotation allowed by implant 100 may be about ±3°. In other embodiments, maximum axial rotation allowed by implant 100 may be about ±1°. Rotation of engaging plate 102 relative to engaging plate 106 may be limited by a height of convex portion 160 relative to a depth of recess 162. In some embodiments, rotation of engaging plate 102 relative to engaging plate 106 may be limited by a curvature of convex portion 160 and/or a curvature of recess 162.

Inner surface 112' of engaging plate 106 may include recess 152. Recess 152 may be complementary in shape to convex portion 150 of member 104. Convex portion 150 may complement recess 152. Convex portion 150 may allow engaging plate 106 to move (e.g., rock) relative to member 104. Movement of engaging plate 106 relative to member 104 may allow lateral movement of the spine. In some embodiments, member 104 may include a recess complementary to a convex portion of engaging plate 106.

Convex portion 150 may have an arcuate cross-sectional shape in an anteroposterior plane and/or in a mediolateral plane. An arcuate shape of convex portion 150 in the anteroposterior plane may allow engaging plate 106 to move relative to member 104 in the directions indicated by arrow 134. Movement of engaging plate 106 relative to engaging plate 102 in the anteroposterior plane may allow flexion and/or extension of the spine. The arcuate shape of convex portion 150 in the mediolateral plane may allow engaging plate 106 to move relative to member 104 in the directions indicated by arrow 136 shown in FIG. 11. Movement of engaging plate 106 relative to member 104 in the mediolateral plane may allow lateral bending of the spine.

Inner surface 112' of engaging plate 106 may contact surface 156 of member 104. Contact of inner surface 112' with surface 156 may limit anterior movement of engaging plate 106 relative to engaging plate 102. Contact of inner surface 112' with surface 156 may therefore limit flexion of vertebrae adjacent to engaging plates 102, 106. A thickness of an edge of member 104 may limit flexion allowed by implant 100. Maximum flexion allowed by implant 100 may range from about 5° to about 20°. In some embodiments, maximum flexion allowed by implant 100 may be about 10°. In other embodiments, maximum flexion allowed by implant 100 may be about 15°.

Figure 14:
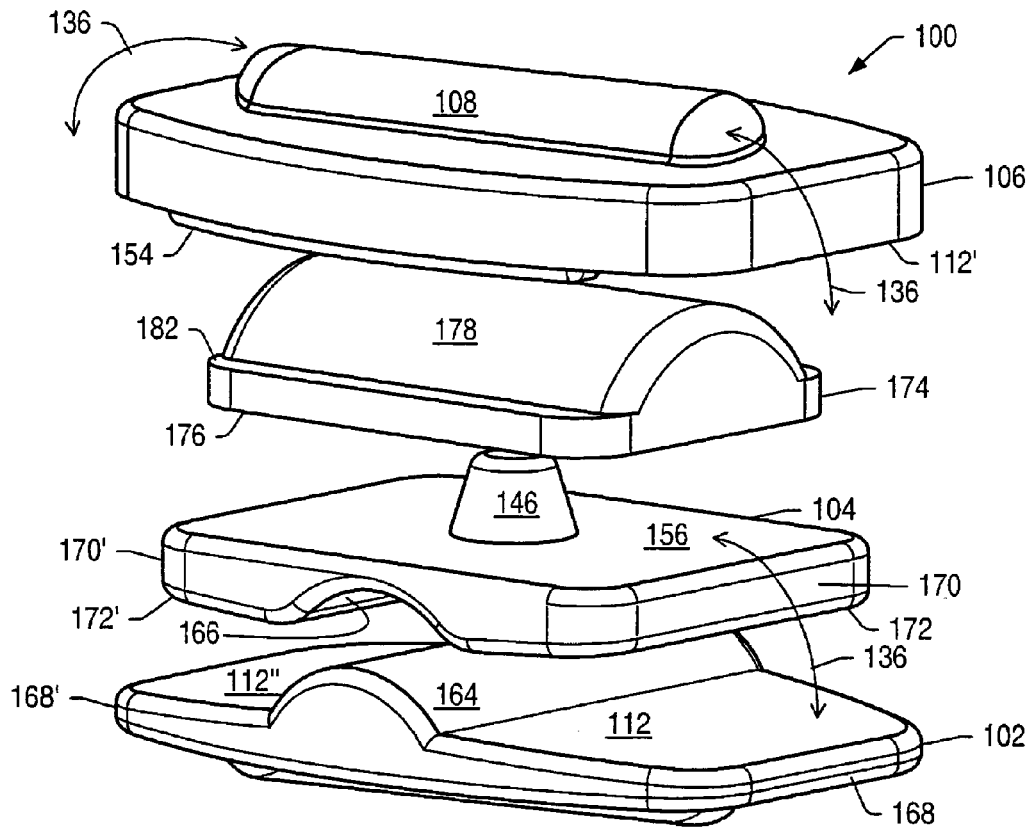
FIG. 14 is a perspective view of components of a disc implant.
Figure 15:
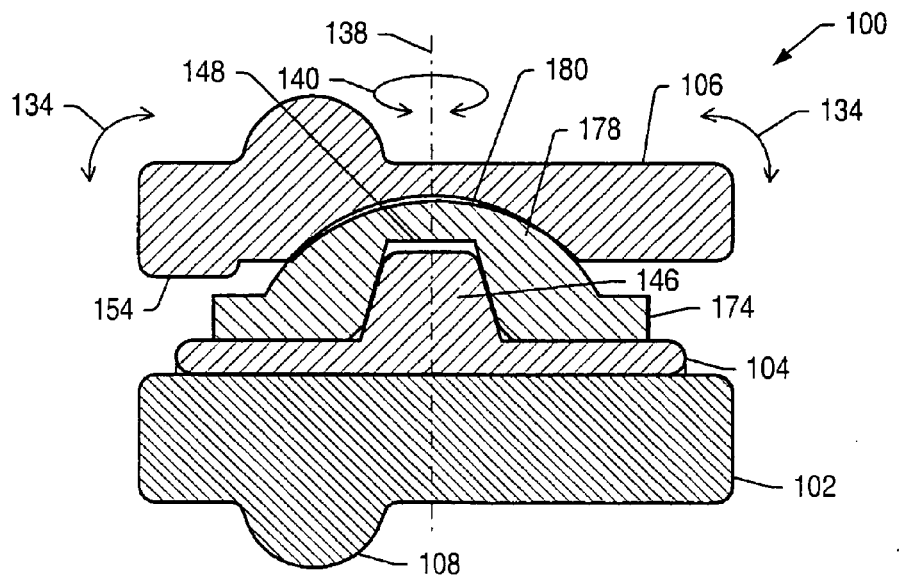
FIG. 15 is a cross-sectional view of an embodiment of a disc implant.
Figure 16:
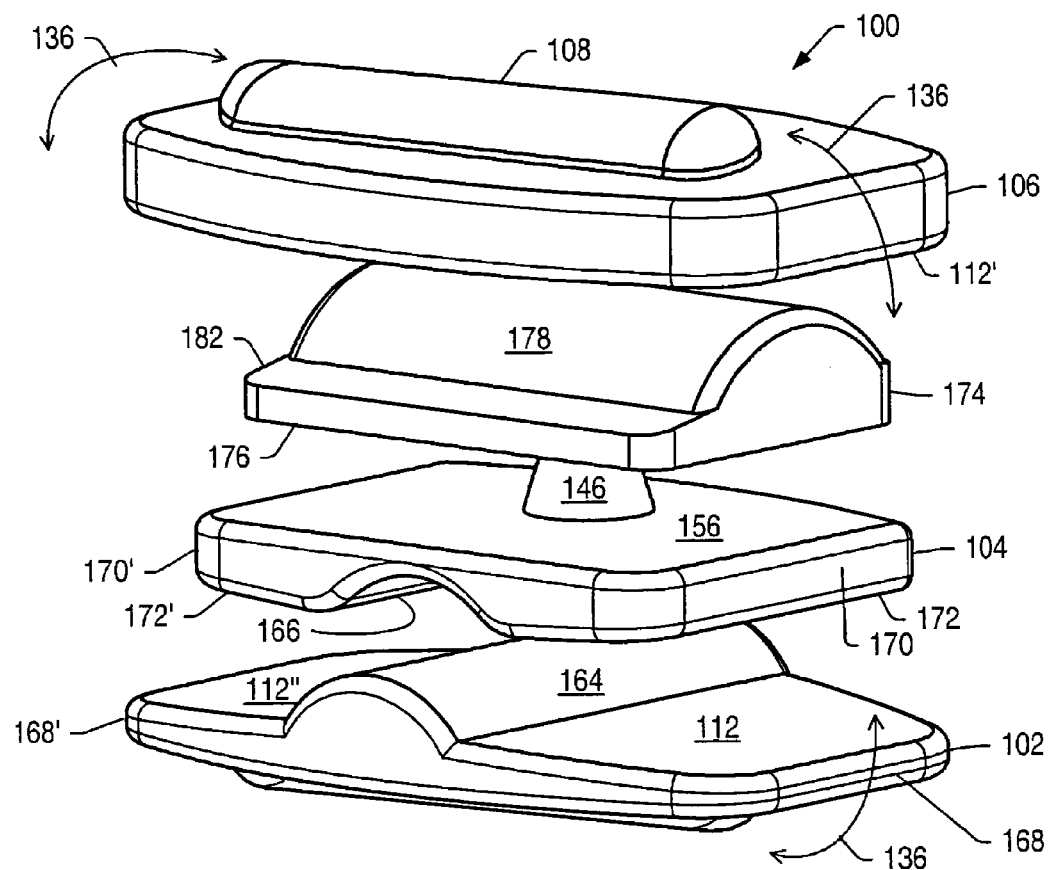
FIG. 16 is a perspective view of components of a disc implant.
Figure 17:
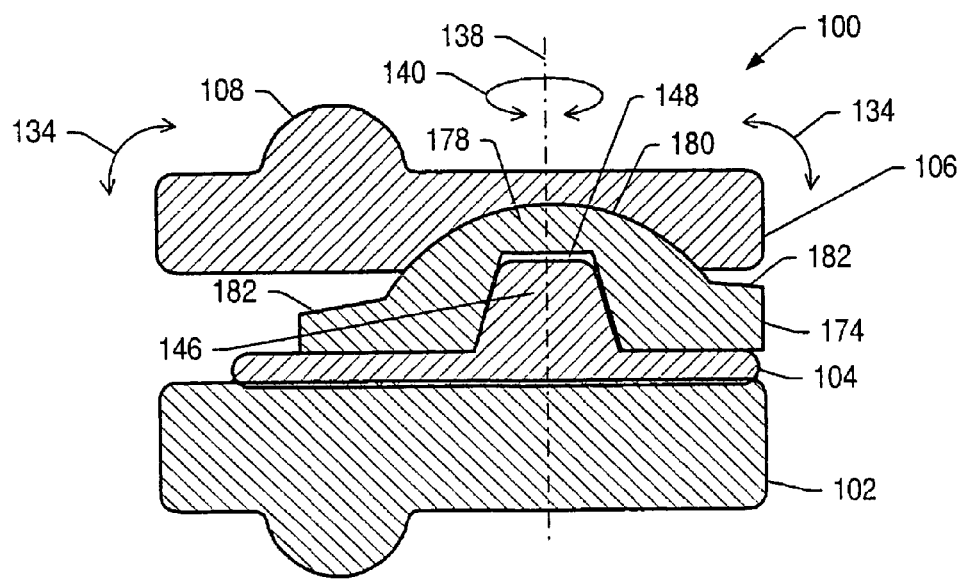
FIG. 17 is a cross-sectional view of an embodiment of a disc implant.

In certain embodiments, disc implant 100 may include two engaging plates and two members as depicted in FIGS. 14 and 16. FIGS. 15 and 17 are cross-sectional views of implants 100 shown in FIGS. 14 and 16, respectively. Engaging plate 102 of implants 100 may have convex portion 164. Convex portion 164 may have an arcuate cross-sectional shape along at least one axis. The arcuate cross-sectional shape along one axis of convex portion 164 may increase an area of contact between engaging plate 102 and member 104. Member 104 may include recess 166. Recess 166 may complement convex portion 164. A shape of convex portion 164 may allow anteroposterior translation of member 104 relative to engaging plate 102. Translation of member 104 relative to engaging plate 102 may allow positioning of implant 100 during a spinal stabilization procedure.

A thickness of engaging plate 102 proximate convex portion 164 may exceed a thickness of engaging plate 102 proximate edges 168, 168' such that inner surfaces 112, 112" are sloped relative to an outer surface of the engaging plate. In some embodiments, a slope of inner surface 112 may be different than a slope of inner surface 112". In certain embodiments, a thickness of member 104 proximate recess 166 may exceed a thickness of the member at edges 170, 170' such that surfaces 172, 172' are sloped relative to surface 156.

Inner surfaces 112, 112" and surfaces 172, 172' may be sloped to allow movement (e.g., rocking) of engaging plate 102 relative to member 104 in a mediolateral plane. Movement of member 104 in the direction indicated by arrow 136 may allow lateral bending of vertebrae adjacent to engaging plates 102, 106. Inner surfaces 112, 112" and surfaces 172, 172' may be sloped such that lateral movement of the spine in a mediolateral plane is restricted. In some embodiments, a slope of surface 172 relative to surface 156 may be different than a slope of surface 172' relative to surface 156. In some embodiments, slopes of surfaces 172, 172' may be opposite in sign to slopes of inner surfaces 112, 112". Movement of engaging plate 102 relative to member 104 may allow inner surfaces 112, 112" to contact surfaces 172, 172'. Contact of inner surfaces 112, 112" and surfaces 172, 172' may distribute a compressive load applied to implant 100 over a relatively large surface area.

Member 104 may include projection 146. Projection 146 may be coupled to member 104. In some embodiments, projection 146 may be an integral part of member 104. A shape of projection 146 may be, but is not limited to being, tapered, round or square. Member 174 may include recess 148, as depicted in FIGS. 15 and 17. Recess 148 may complement projection 146. Recess 148 may have a slightly larger cross section than projection 146 to allow relative movement of members 104, 174. In some embodiments, member 174 may rotate relative to member 104 about axis of rotation 138 indicated by arrow 140. As shown in FIG. 15, axis of rotation 138 may be near a center of implant 100. In some embodiments, axis of rotation 138 may be located more off-center, as depicted in FIG. 17. A range of rotation of member 174 relative to member 104 may be limited by a size and/or shape of recess 148 relative to a size and/or shape of projection 146.

Surface 176 of member 174 may contact surface 156 of member 104 when projection 146 fits in recess 148. A relatively large contact area between member 104 and member 174 may distribute an effective load applied to implant 100 while allowing rotation of vertebrae adjacent to the implant. For example, projection 146 (shown in FIG. 14) has a flat surface that may increase a contact area between projection 146 and recess 148. Reducing friction between member 104 and member 174 may allow facile rotation of the members relative to each other.

Member 174 may have convex portion 178. Convex portion 178 may have an arcuate cross-sectional shape in an anteroposterior plane. Engaging plate 106 may include recess 180 (shown in FIG. 15 and FIG. 17). Recess 180 may be concave with an arcuate cross-sectional shape in an anteroposterior plane. Recess 180 may complement convex portion 178 of member 174. In some embodiments, recess 180 may have a slightly larger cross section than convex portion 178 to allow movement of engaging plate 106 relative to member 174. Movement of engaging plate 106 relative to member 174 may allow for flexion and/or extension of vertebrae adjacent to the engaging plates in the plane indicated by arrows 134 in FIGS. 15 and 17.

In some embodiments, anteroposterior and/or lateral movement of components of implant 100 relative to each other may be limited. As shown in FIGS. 14 and 15, engaging plate 106 may include limiter 154. Limiter 154 may be a projection extending from inner surface 112' of engaging plate 106. In an embodiment, limiter 154 may extend along a side of engaging plate 106. Limiter 154 may be positioned to contact surface 182 of member 174 when engaging plate 106 rocks in a posterior direction toward engaging plate 102. Increasing a length of limiter 154 may increase an area of contact between limiter 154 and member 174. Increasing the area of contact between limiter 154 and member 174 may distribute a compressive load on implant 100 over a relatively large area. Distributing the load over a relatively large area may reduce stress among components of implant 100.

Contact of limiter 154 with surface 182 may limit movement of engaging plate 106 relative to member 174. A height of limiter 154 relative to inner surface 112' and/or a distance between surfaces 176 and 182 of member 174 may be chosen to limit movement of engaging plate 106 relative to member 174. In certain embodiments, surface 182 of member 174 may be sloped relative to surface 176 to increase an area of contact between surface 182 and limiter 154. Surface 182 may be sloped to increase a range of motion between engaging plate 106 and member 174. In some embodiments, a slope of surface 182 may limit movement of engaging plate 106 relative to member 174. In certain embodiments, maximum extension allowed by implant 100 may range from about 3° to about 12°. In some embodiments, maximum extension allowed by implant 100 may be about 8°. In other embodiments, maximum extension allowed by implant 100 may be about 5°. Some implant embodiments may include a limiter designed to limit another component of motion of a disc implant. Other implant embodiments may include one or more additional limiters designed to limit other components of motion of a disc implant.

In certain embodiments, inner surface 112' of engaging plate 106 may contact surface 182 of member 174. Contact of inner surface 112' with surface 182 may limit flexion of vertebrae adjacent to engaging plates 102, 106. A distance between surfaces 176 and 182 of member 174 may be chosen to limit flexion between vertebrae adjacent to engaging plates 102, 106. Maximum flexion allowed by implant 100 may range from about 5° to about 20°. In some embodiments, maximum flexion allowed by implant 100 may be about 10°. In other embodiments, maximum flexion allowed by implant 100 may be about 15°.

In certain embodiments, components of implant 100 may be coupled to one another. Coupling of components of implant 100 may allow partial assembly of the implant prior to a surgical procedure. In some embodiments, a manufacturer of implant 100 may at least partially assemble the implant prior to shipment. Some of the components of implant 100 may be held together during use, at least partially, by pressure resulting from the natural compression of the spine.

Figure 18:
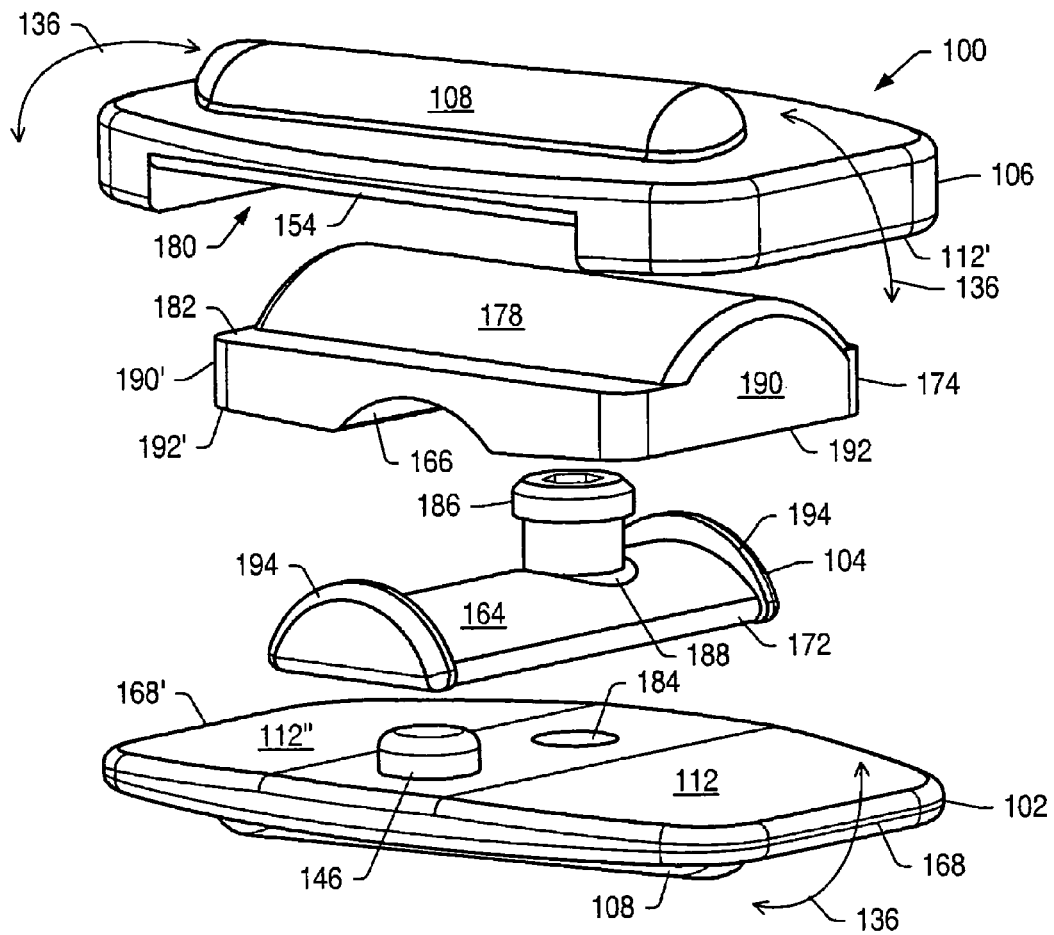
FIG. 18 is a perspective view of components of a disc implant.
Figure 19:
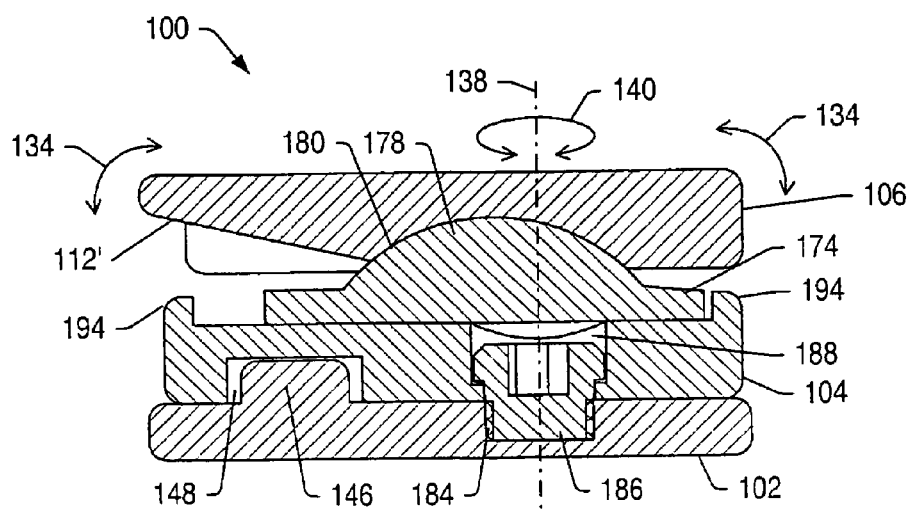
FIG. 19 is a cross-sectional view of an embodiment of a disc implant.

FIG. 18 depicts a perspective view of components of implant 100, including engaging plate 102, members 104 and 174, and engaging plate 106. FIG. 19 depicts a cross-sectional view of the implant shown in FIG. 18 after the implant has been assembled. As shown in FIGS. 18 and 19, engaging plate 102 may include projection 146 and opening 184. Projection 146 may be coupled to engaging plate 102. In some embodiments, projection 146 may be an integral part of engaging plate 102. A shape of projection 146 may be, but is not limited to being, round, square, rectangular or irregular. Projection 146 may complement recess 148 (shown in FIG. 19) in member 104. In certain embodiments, recess 148 may have a slightly larger cross section than projection 146 to allow engaging plate 102 to move relative to member 104. In some embodiments, recess 148 may have a cross section substantially equal to a cross section of projection 146 to inhibit rotation of engaging plate 102 relative to member 104.

In some embodiments, opening 184 may extend through engaging plate 102. In other embodiments, opening 184 may extend to a fixed depth in engaging plate 102. Opening 184 may be designed (e.g., threaded) to receive a coupling device such as coupler 186. Coupler 186 may be, but is not limited to being, a screw, a bolt or a pinch clamp. Coupler 186 may couple member 104 to engaging plate 102. During use, coupler 186 may extend through at least a portion of member 104 into opening 184 of engaging plate 102. A head of coupler 186 may be recessed in opening 188 of member 104. Coupler 186 may allow engaging plate 102 to move relative to member 104. In some embodiments, engaging plate 102 may rotate around axis of rotation 138 relative to first member 104 in the plane indicated by arrow 140 in FIG. 19. Relative movement of engaging plates 102, 106 may allow axial rotation of vertebrae adjacent to implant 100. Axis of rotation 138 may be offset from a center of engaging plates 102, 106 to imitate a longitudinal axis of rotation of a spine.

Figure 20:
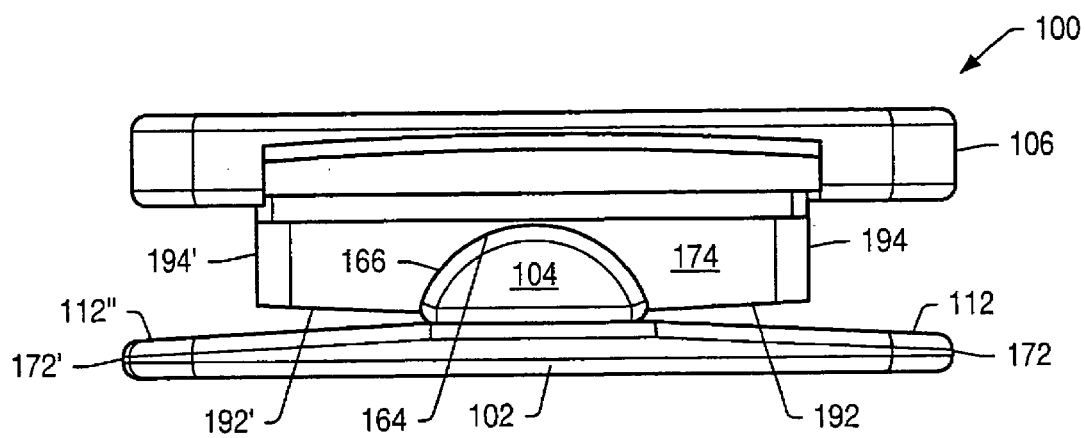
FIG. 20 is a side view of an embodiment of a disc implant.

As shown in FIG. 18, member 104 may have convex portion 164. Convex portion 164 may have an arcuate cross-sectional shape along at least one axis. Member 174 may include recess 166. Recess 166 may have an arcuate cross section along at least one axis. Recess 166 may complement convex portion 164 of member 104, as shown in the side view of implant 100 in FIG. 20. In some embodiments, a thickness of engaging plate 102 proximate member 104 may exceed a thickness of the engaging plate at ends 168, 168' such that inner surfaces 112, 112" slope toward an outer surface of the engaging plate. In some embodiments, a slope of inner surface 112 may be different than a slope of inner surface 112". A thickness of member 174 proximate recess 166 may exceed a thickness of the member at ends 190, 190' such that surfaces 192, 192' of second member 174 slope away from engaging plate 102. In some embodiments, a slope of surface 192 may be different than a slope of surface 192'. In some embodiments, slopes of surfaces 192, 192' may be substantially the same magnitude as slopes of inner surfaces 112, 112", respectively.

Sloped surfaces 112, 112" may allow engaging plate 102 to move (e.g., rock) relative to member 104 in a mediolateral plane. Relative movement of engaging plates 102, 106 may allow lateral bending of vertebrae adjacent to the engaging plates in the plane indicated by arrow 136 in FIG. 18. Contact of surfaces 112, 112" and 192, 192', respectively, may distribute a compressive load applied to implant 100 over a relatively large area.

In some embodiments, member 174 may have convex portion 178. Convex portion 178 may have an arcuate cross-sectional shape. Engaging plate 106 may include recess 180. Recess 180 may be concave with an arcuate cross-sectional shape. Recess 180 may complement convex portion 178. Recess 180 may have a slightly larger cross section than convex portion 178 to allow engaging plate 106 to move (e.g., rock) toward engaging plate 102 as indicated by arrow 134 in FIG. 19. Movement of engaging plate 106 relative to member 174 may allow flexion and/or extension of vertebrae adjacent to engaging plates 102, 106.

Member 104 may include one or more stops 194 (shown in FIGS. 18 and 19). Stops 194 may be coupled to one or both ends of member 104. In some embodiments, stops 194 may be an integral part of member 104. Stops 194 may restrict anteroposterior translation of member 174 relative to member 104. Restriction of translation of member 174 relative to member 104 may facilitate positioning of implant 100 between vertebrae.

In certain embodiments, contact of stop 194 with inner surface 112' of engaging plate 106 may limit extension of vertebrae adjacent to implant 100. A height of stop 194 and/or a thickness of engaging plate 106 may limit extension allowed by implant 100. Maximum extension allowed by implant 100 may range from about 3° to about 12°. In some embodiments, maximum extension allowed by implant 100 may be about 8°. In other embodiments, maximum extension allowed by implant 100 may be about 5°.

Surface 182 of member 174 may be sloped relative to surfaces 192, 192' of the member. Inner surface 112' of engaging plate 106 may be sloped relative to an outer surface of the engaging plate. A slope of surface 182 and/or a slope of inner surface 112' may be chosen to increase a contact area between surface 182 and limiter 154 of engaging plate 106. A slope of surface 182 may be chosen to increase a range of motion between engaging plate 106 and member 174. In some embodiments, a shape and/or size of recess 180 may limit motion of engaging plate 106 relative to another component of the implant.

In certain embodiments, inner surface 112' of engaging plate 106 may contact surface 182 of member 174. Contact of inner surface 112' and surface 182 may limit flexion of the spine. A distance between surface 182 and surfaces 192, 192' of member 174 may be chosen to limit flexion between vertebrae adjacent to engaging plates 102, 106. Maximum flexion allowed by implant 100 may be from about 5° to about 20°. In some embodiments, maximum flexion allowed by implant 100 may be about 10°. In other embodiments, maximum flexion allowed by implant 100 may be about 15°.

Figure 21:
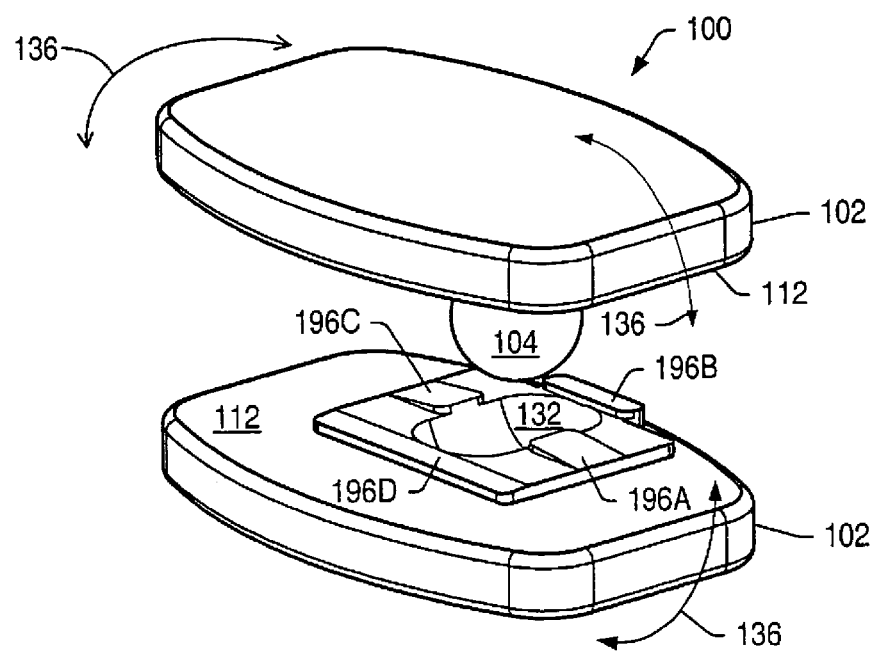
FIG. 21 is a perspective view of an embodiment of a disc implant.

In some embodiments, a first engaging plate may be substantially the same as a second engaging plate. Manufacturing costs may be reduced for implants with substantially equivalent engaging plates. FIG. 21 depicts a perspective view of implant 100 with substantially equivalent engaging plates 102. Member 104 may separate engaging plates 102. In certain embodiments, member 104 may have a rounded shape including, but not limited to, ovoid, spheroid and ellipsoid. Member 104 may be formed from metal (e.g., chrome) or ceramic. In certain embodiments, member 104 may be highly polished to inhibit wear. Engaging plates 102 may include concave portions 132. Concave portions 132 may complement member 104. A thickness of member 104 may exceed a cumulative depth of concave portions 132.

Figure 22:
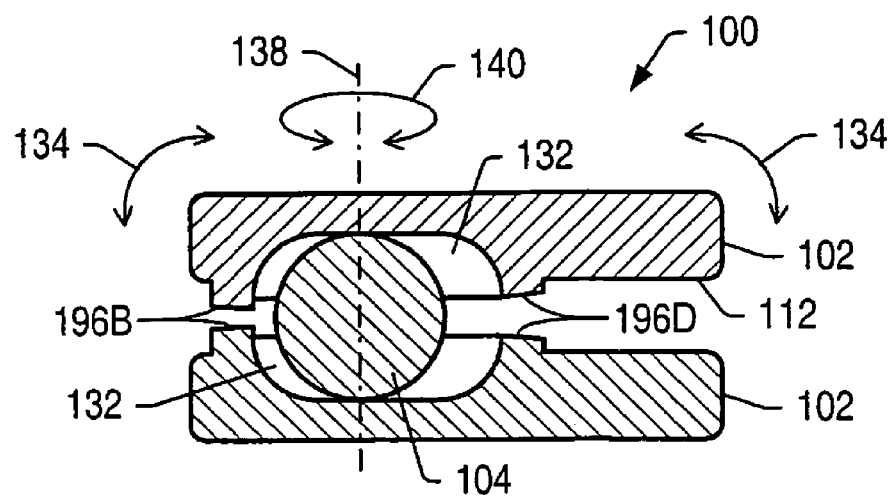
FIG. 22 is a cross-sectional view of an embodiment of a disc implant.

FIG. 22 depicts a cross-sectional view of the implant shown in FIG. 21 after the implant has been assembled. A separation of engaging plates 102 by member 104 may allow the engaging plates to "rock" relative to one another. Rocking of engaging plates 102 relative to one another in an anteroposterior plane may allow flexion and/or extension in the plane indicated by arrows 134. Rocking of engaging plates 102 relative to one another in a mediolateral plane may allow lateral bending in the plane indicated by arrows 136 in FIG. 21.

A shape of member 104 may provide a large contact area between the surface of member 104 and concave portions 132. A shape of member 104 may decrease wear and/or failure of implant 100. Concave portions 132 with an oval shape may allow member 104 to imitate the movement of a human spine around axis of rotation 138. Engaging plates 102 may freely rotate relative to one another around axis of rotation 138 in the plane indicated by arrow 140. In some embodiments, a position of axis of rotation 138 may change as member 104 translates in recesses 132. In an embodiment, a range of motion (e.g., axial rotation) may be limited by the shape of member 104 and/or the shape of concave portion 132.

In an embodiment, an inner surface of engaging plates 102 proximate concave portions 132 may be elevated An elevation of one or more surfaces 196A-196D (shown in FIG. 21) may be chosen to limit relative movement of engaging plates 102. One or more surfaces 196A-196D may be sloped relative to outer surfaces of engaging plates 102 as shown in FIGS. 21 and 22. Slopes of surfaces 196A-196D may increase a contact area between engaging plates 102. Increasing a contact area between engaging plates 102 may inhibit wear of the implant.

In certain embodiments, surfaces 196D may limit flexion of vertebrae adjacent to the spinal implant. Surfaces 196B may limit extension of vertebrae adjacent to implant 100. Surfaces 196A and 196C may limit lateral bending of vertebra adjacent to implant 100. In some embodiments, axial rotation of engaging plates 102 relative to each other may be limited.

In some embodiments, an implant may be curved to accommodate radial curvature of vertebrae. Implants may be provided with varying amounts of radial curvature. For example, disc implants may be provided with large, medium and/or small radial curvatures. An indication of an amount of radial curvature provided by an implant may be etched or otherwise marked on the implant.

In some disc implant embodiments, engaging plates may be sloped to establish a desired lordotic curvature of a spine. Several different implant components with differing lordotic curvatures may be available to a surgeon so that the surgeon can form an implant with a desired lordotic angle. Lordotic indications may be etched or otherwise marked (e.g., color coded) on the disc implant to indicate the amount of lordosis that the implant will provide. In an embodiment, a lumbar disc implant may have a lordotic angle range of about 5° to about 20° (e.g., about 12°).

An engaging plate may be designed to promote coupling of the engaging plate to a vertebral surface. Coupling engaging plates of an implant to adjacent vertebrae may stabilize the disc implant. An engaging plate may include one or more coupling projections to facilitate coupling of the engaging plate to a vertebra. A coupling projection may extend from an outer surface of an engaging plate. Coupling projections may be, but are not limited to being, press fit, welded, glued or otherwise affixed to an engaging plate. Alternatively, coupling projections may be formed as part of an engaging plate. Any combination of coupling projections 108 may be used together to ensure stability of implant 100.

Figure 23:
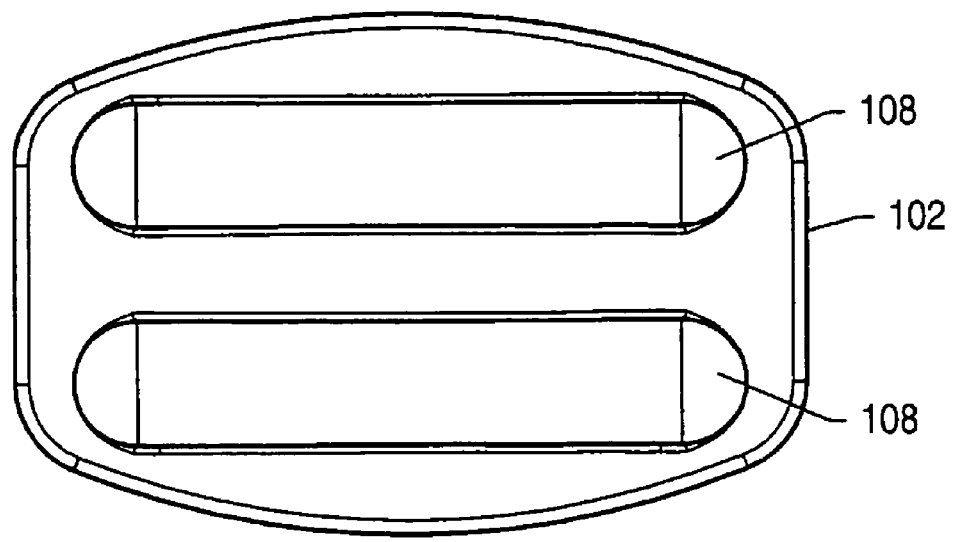
FIGS. 23-27 depict embodiments of coupling projections.
Figure 24:
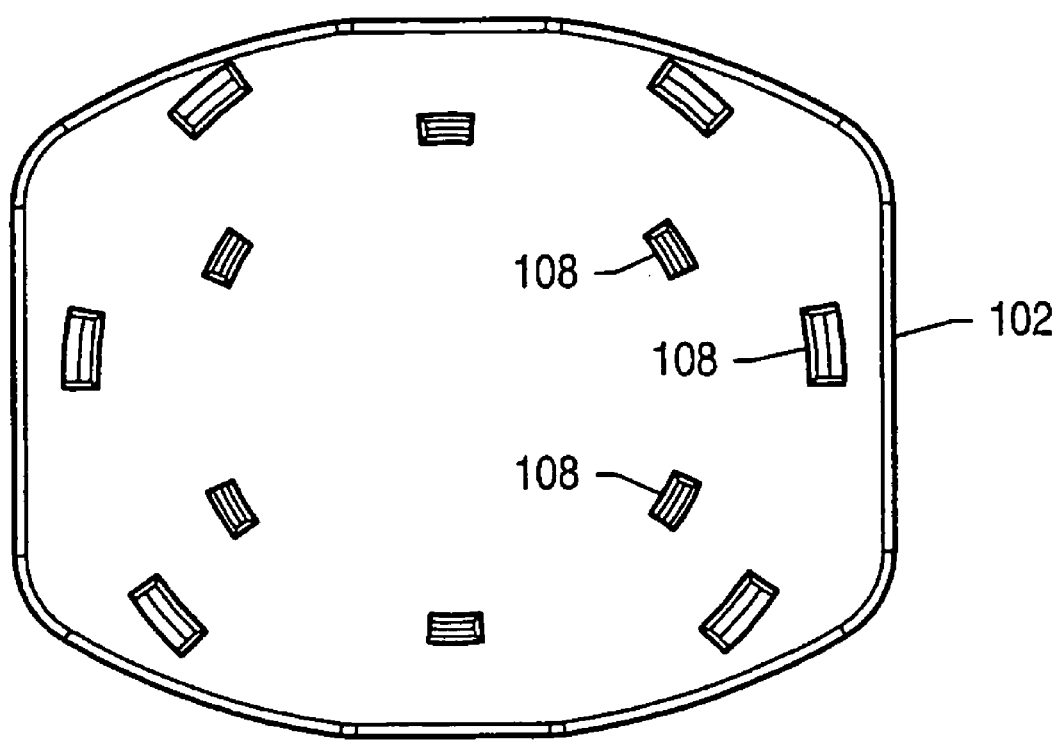
Figure 25:
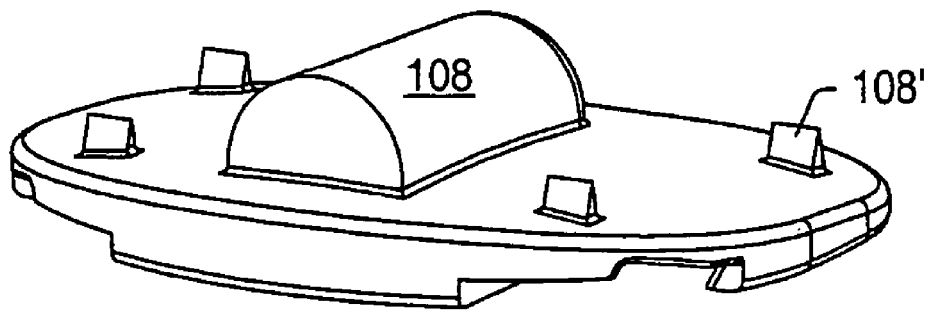

An engaging plate may include one coupling projection 108, as shown, for example, in FIGS. 9-11. FIG. 23 depicts a view of engaging plate 102 with two coupling projections 108. In some embodiments, an engaging plate may include a plurality of coupling projections 108, as shown in FIGS. 24 and 25. In some embodiments, an engaging plate may include coupling projections of substantially the same shape and size. In certain embodiments, an engaging plate may include coupling projections of different sizes and/or shapes. A shape and/or size of a coupling projection may be chosen based on factors including, but not limited to, durability, distribution of load and ease of forming a complementary recess in a vertebra.

Figure 26:
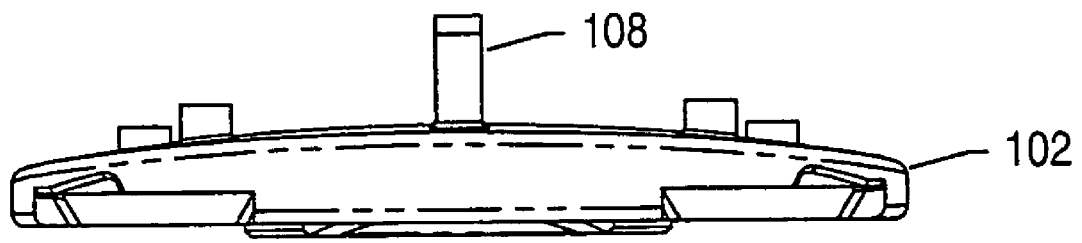
Figure 27:
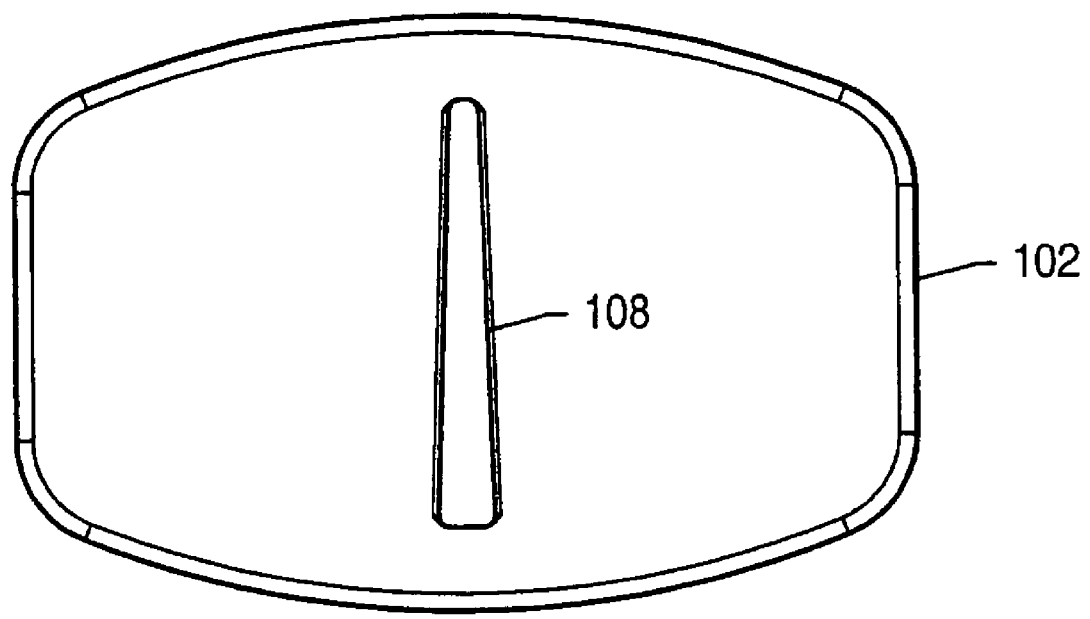

In certain embodiments, a coupling projection extending from an engaging plate may be positioned in a recess formed in a vertebra. The recess may complement the coupling projection. Coupling projection 108 may have an arcuate cross section, as depicted, for example, in FIGS. 9-11. In some embodiments, a coupling projection may have a square or rectangular cross section. FIG. 26 depicts a view of coupling projection 108 with a rectangular cross section. In certain embodiments, a coupling projection may be tapered in one or more directions. Coupling projection 108 shown in FIG. 27 is tapered in an anteroposterior direction. A tapered coupling projection may allow the coupling projection to be wedged into a recess in a bone to secure the engaging plate to the bone. Wedging the coupling projection in the recess may inhibit movement of the engaging plate relative to the vertebra and/or expulsion of the engaging plate from the bone. In some embodiments, surfaces of the coupling projection that are to be positioned adjacent to bone may be roughened or include a coating (e.g., hydroxyapatite) to promote osseointegration of the coupling projection with the bone. In some embodiments, coupling projections, such as those depicted in FIGS. 1, 24 and 25, may penetrate adjacent bone to inhibit movement of the engaging plate relative to the vertebra and/or to inhibit expulsion of the engaging plate from the bone.

In some embodiments, one or more coupling projections may be oriented substantially in an anteroposterior plane to facilitate implant insertion using an anterior approach. In some embodiments, one or more coupling projections may be oriented substantially in a mediolateral plane to facilitate implant insertion using a lateral approach. In certain embodiments, combinations of coupling projections of various cross-sectional shapes, such as those depicted in FIG. 1 may be used to inhibit movement of the engaging plate relative to the vertebra and/or expulsion of the engaging plate from the bone.

In some embodiments, a fastening system may be used to couple an implant to a vertebra. The implant may include a tab with an opening in a face of the tab. The opening may engage or couple to a head of a bone fastener. A fastening system may include a fastener and a locking mechanism. The locking mechanism may be positioned between the implant and the fastener. The locking mechanism may inhibit backout of the fastener from the vertebra and from the implant. In some embodiments, the locking mechanism may be a ring positioned in an opening in the implant. When the ring is in the opening, a head of the fastener inserted through the ring may contact the ring if the fastener begins to back out of the opening. The ring and fastener head combination may be too large to exit the opening, thereby inhibiting backout of the fastener from the vertebrae and from the implant. When the ring is positioned in the opening, the ring may lock to the fastener head without locking to the implant, thus allowing the plate to be securely tightened to the vertebra. U.S. Pat. No. 6,454,769 to Wagner et al. and U.S. Pat. No. 6,331,179 to Freid et al., both of which are incorporated by reference as if fully set forth herein, describe fastening systems including locking mechanism for inhibiting backout of fasteners.

In certain embodiments, one or more instruments may be used to insert and/or position a disc implant between adjacent vertebrae after a discectomy has been performed. An inserter may be used to position an implant in a prepared disc space between adjacent vertebrae. The inserter may be sufficiently long to allow placement of a distal end of the inserter in the disc space from above an incision in a patient. Engaging plates of an implant may be coupled to arms at the distal end of the inserter.

Figure 28:
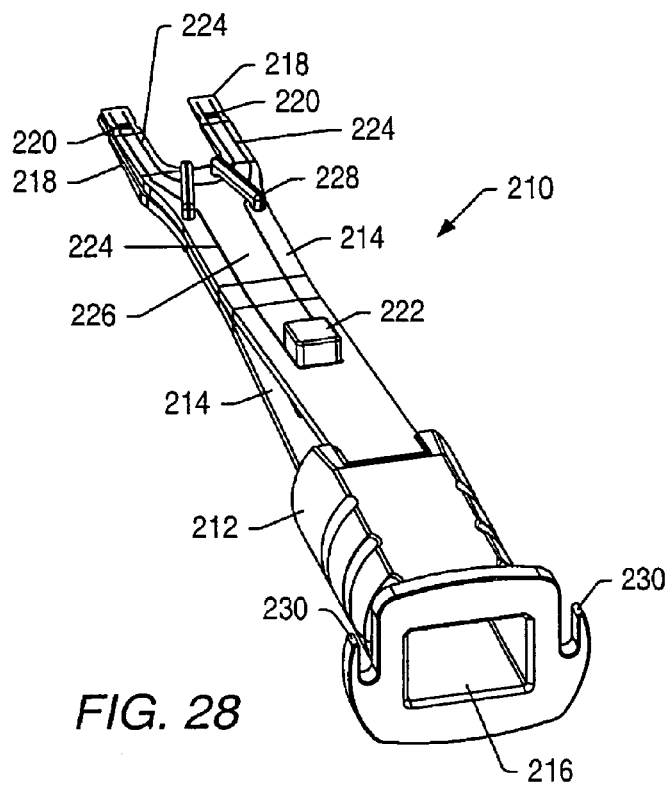
FIG. 28 is a perspective view of an embodiment of an inserter.
Figure 29:
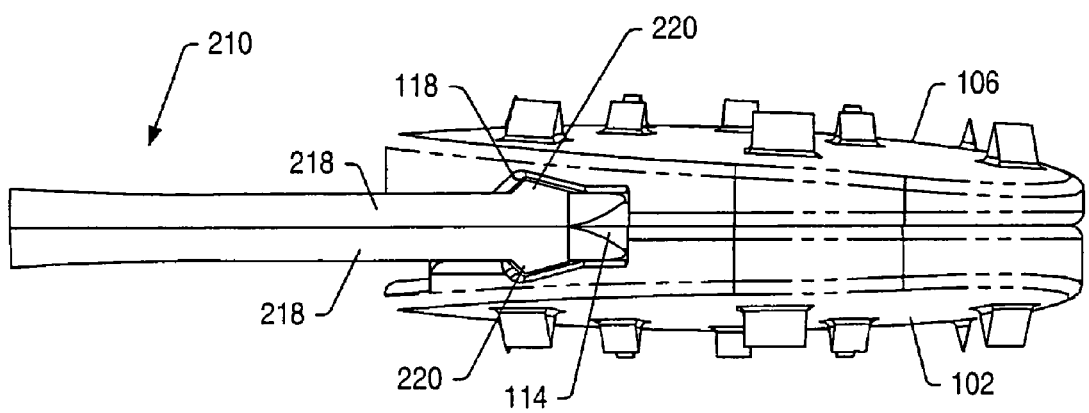
FIG. 29 is a side view of a portion of an embodiment of an inserter coupled to engaging plates.

FIG. 28 depicts a perspective view of an embodiment of inserter 210. Inserter 210 may include body 212 and arms 214. Body 212 may have opening 216. Opening 216 may be sized to allow one or more guidance, insertion and/or removal instruments to be positioned in inserter 210. Arms 214 may include extensions 218 for coupling inserter 210 to engaging plates of an implant. Extensions 218 may be chamfered, rounded, dovetailed or otherwise machined to engage slots 114 in engaging plates 102, 106 (shown in FIG. 1). Extensions 218 may include detents 220. Detents 220 may be positioned in indents 118 of engaging plates 102, 106 to couple inserter 210 to an implant. FIG. 29 depicts extensions 218 coupled to engaging plates 102, 106.

Portions of arms 214 may be angled relative to each other to establish a tapering separation distance between the arms. The angled portions of arms 214 may facilitate insertion of instruments that establish a desired separation distance between engaging plates 102, 106 attached to inserter 210.

Figure 30:
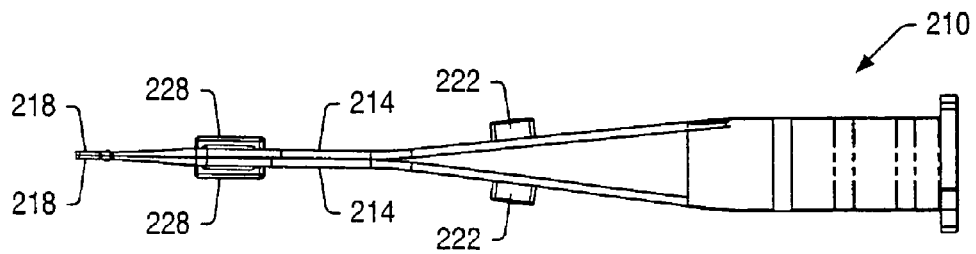
FIG. 30 is a side view of an embodiment of an inserter.

Arms 214 may include mechanisms 222. FIG. 30 depicts a perspective side-view of inserter 210 that shows mechanisms 222 on arms 214. As depicted in FIG. 28, inserter 210 may include slots 224. Slots 224 may extend through arms 214 and extensions 218 from the mechanism 222 to a portion of the inserter near detents 220. Slots 224 may allow section 226 of inserter 210 to bend. Pressing mechanisms 222 may move section 226 and allow disengagement of detents 220 from indents located in engaging plates. When mechanisms 222 are pressed, detents may be disengaged from indents in engaging plates to separate inserter 210 from the engaging plates. In some embodiments, arms 214 may include reinforcement members 228 that stabilize portions of the inserter that are not able to move when mechanisms 222 are pressed. Reinforcement members 228 may limit outward movement of sections 226.

Figure 31:
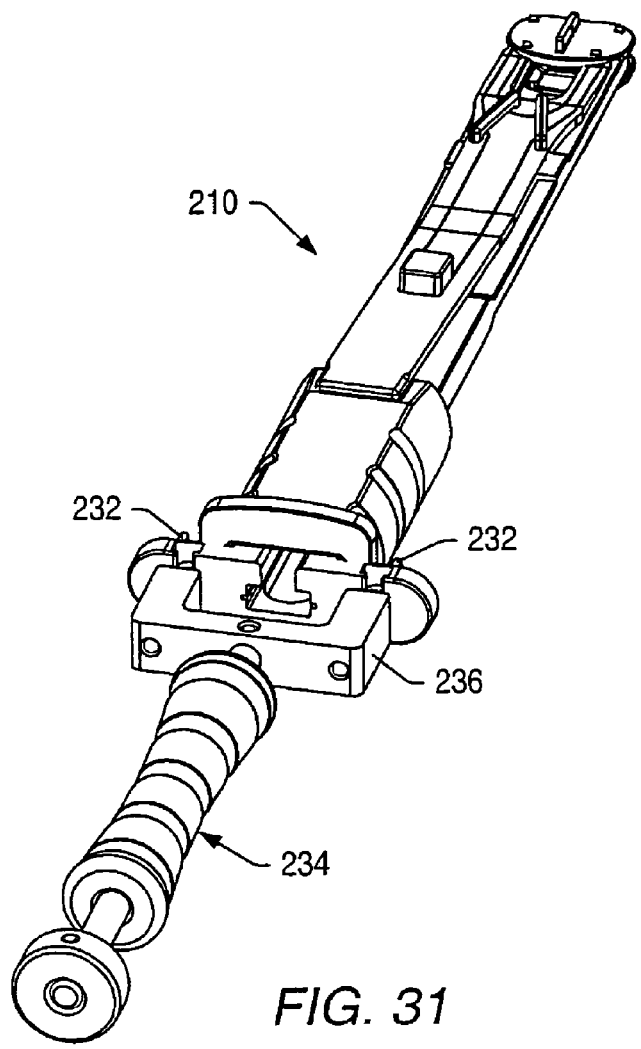
FIG. 31 is a perspective view of an embodiment of a slap hammer coupled to an inserter.

A proximal end of inserter 210 may be formed to engage a driving instrument or a guidance instrument, such as a slap hammer or a pusher. Slots 230 in a proximal end of inserter 210 (shown in FIG. 28) may be machined or otherwise designed to receive a coupling device such as coupler 232 shown in FIG. 31. FIG. 31 depicts a perspective view of inserter 210 coupled to slap hammer 234. Coupler 232 may engage an attachment mount of a driving instrument or a guidance instrument. Slap hammer 234 may include attachment mount 236. Coupler 232 may couple attachment mount 236 to inserter 210.

During some implant insertion procedures, an intervertebral space may be too small to allow insertion of implant components coupled to an inserter without scarring the surfaces of adjacent vertebrae. Shims may be placed adjacent to the vertebrae. Engaging plates coupled to an inserter may be positioned next to the shims. The inserter may be driven downwards to separate the vertebrae and insert the engaging plates between the vertebrae. After insertion of the engaging plates, the shims may be removed.

Figure 32:
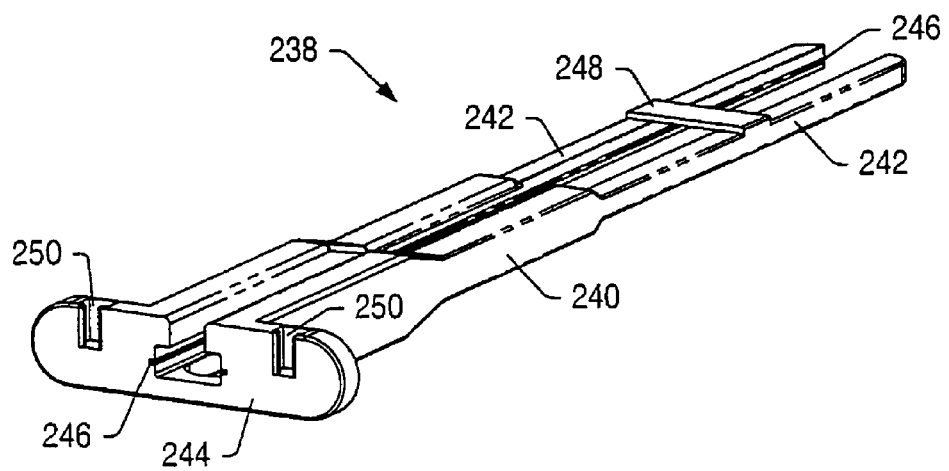
FIG. 32 is a perspective view of an embodiment of a distractor.

In some embodiments, a distractor may be used to separate adjacent vertebrae and/or to separate engaging plates to allow insertion of a member between the engaging plates. FIG. 32 depicts a perspective view of an embodiment of a distractor. Distractor 238 may include body 240, arms 242 and attachment mount 244. Body 240 and arms 242 may include grooves 246. Grooves 246 may be slightly larger in cross-section than projections 128 of member 104 (shown in FIG. 1). Projections 128 of member 104 may fit in grooves 246 to allow member 104 to be guided through body 240 and arms 242 to a position between engaging plates.

In some embodiments, grooves 246 may be sized and/or shaped to accept only a particular sized member of an implant. For example, a member for a 13 mm implant will not fit in a distractor that establishes a separation distance sized for an 11 mm implant. In some embodiments, members and distractors may be color coded substantially the same color. A surgeon may know to only put a member into a distractor of substantially the same color.

In certain embodiments, arms 242 may include reinforcement member 248. Reinforcement member 248 may inhibit movement of arms 242 during insertion of a member between engaging plates to form an implant.

Slots 250 on attachment mount 244 may be machined to receive a coupler. A coupler may couple distractor 238 to a drive instrument, such as a slap hammer.

Figure 33:
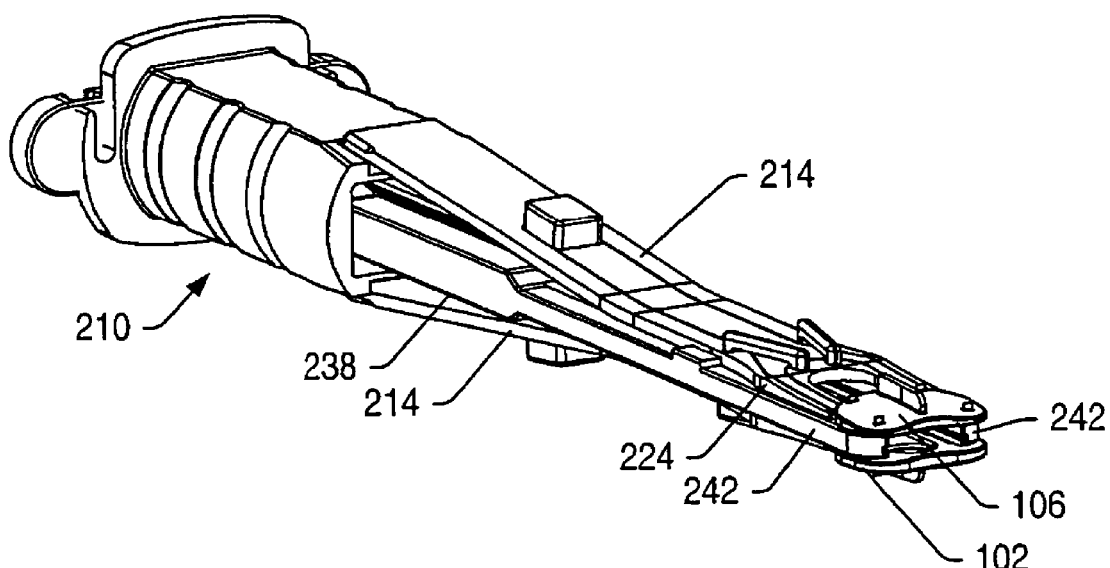
FIG. 33 is a perspective view of an embodiment of a distractor positioned in an inserter.

FIG. 33 depicts a perspective view of distractor 238 positioned in inserter 210. Arms 242 may separate arms 214 of inserter 210. As arms 214 are separated by distractor 238, engaging plates 102, 106 are separated. Slots in engaging plates 102, 106 and arms 242 may separate arms 214 such that the engaging plates remain substantially parallel during the separation process. Engaging plates 102, 106 may remain substantially parallel during insertion of a member between the engaging plates. Separation of arms 214 with distractor 238 may minimize or eliminate contact of the distractor with engaging plates 102, 106. Minimizing or eliminating contact of distractor 238 with engaging plates 102, 106 during distraction may inhibit undesired separation of the engaging plates from the inserter 210.

Figure 34:
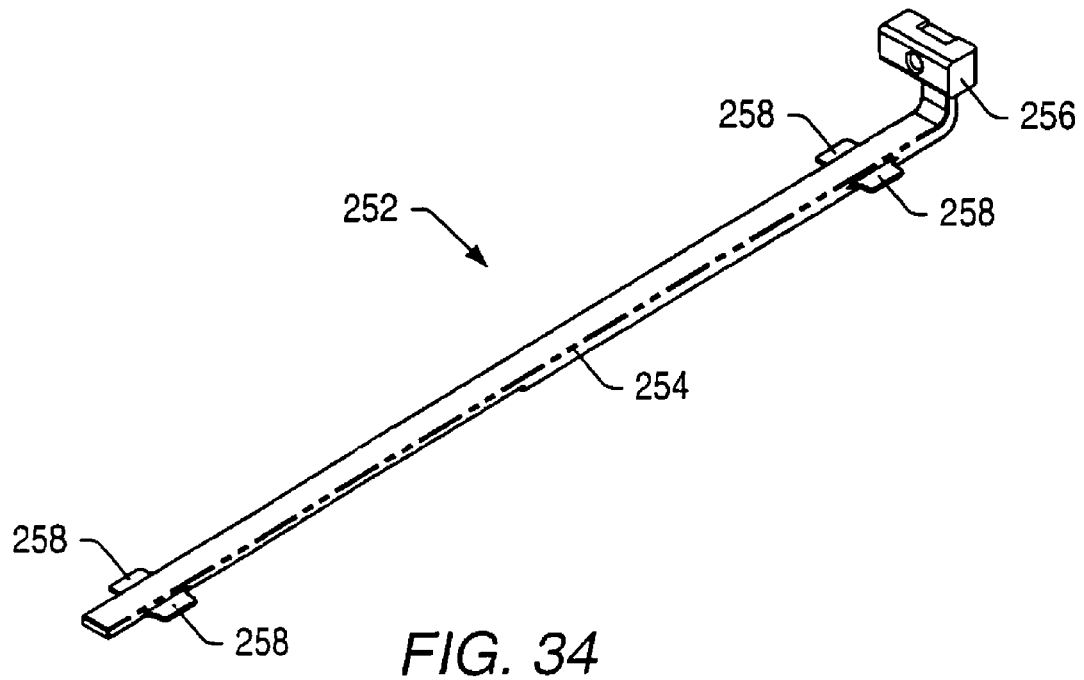
FIG. 34 is a perspective view of an embodiment of a pusher.

FIG. 34 depicts a perspective view of an embodiment of a pusher. Pusher 252 may include body 254 and attachment mount 256. A width of a distal end of body 254 may be less than a width of a proximal end of the body. Body 254 may include projections 258. Projections 258 may fit in grooves 246 of distractor 238 (shown in FIG. 32) to allow pusher 252 to be guided through body 240 and arms 242 of the distractor. In some embodiments, pushers may be color coded to match to a particular size of distractor. In some embodiments, projections 258 may be sized so that the pusher fits in any size of distractor.

Figure 35:
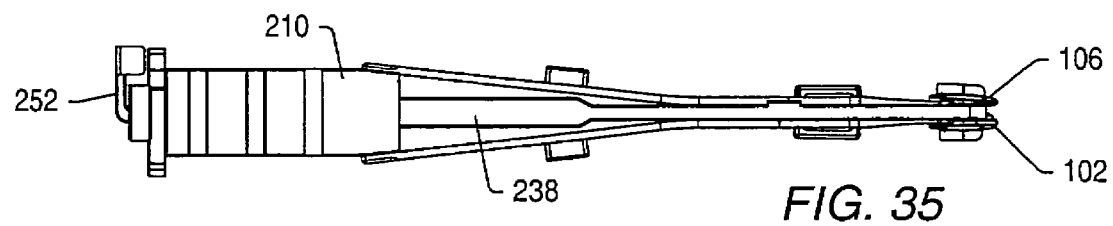
FIG. 35 is a side view of an embodiment of a pusher coupled to an inserter.

Pusher 252 may be used to move a member through distractor 238 to a desired position between engaging plates. FIG. 35 depicts a side view of an embodiment of pusher 252 positioned in distractor 238 and inserter 210. When pusher 252 is positioned in inserter 210, the pusher may maintain a position of a member between engaging plates 102, 106 and allow for removal of distractor 238 from the engaging plates.

During some implant insertion procedures, a channel or channels may be formed in vertebrae. The channel or channels may correspond to a coupling projection or coupling projections of engaging plates. Instrument guides may be used to facilitate formation of a channel or channels in vertebrae. In some embodiments, two instrument guides may be coupled to an inserter. The instrument guides may be inserted into a disc space. A distractor may be introduced into the inserter to move the instrument guides against vertebrae. Channels may be formed in the vertebrae using instruments in combination with the instrument guides.

Figure 36:
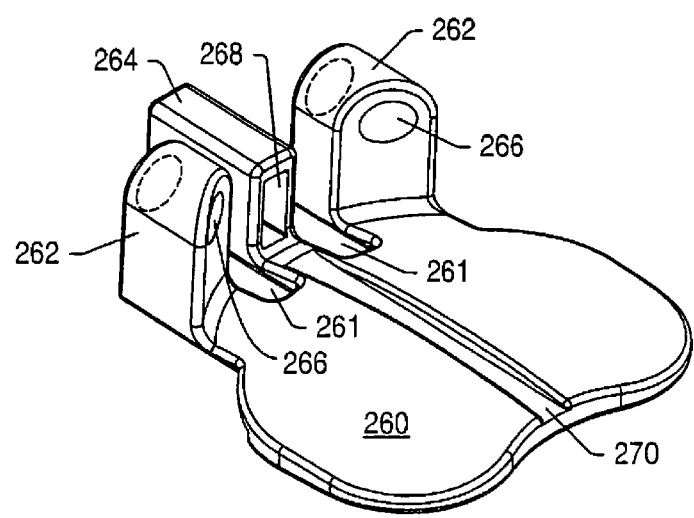
FIG. 36 is a perspective view of an embodiment of an instrument guide.

FIG. 36 depicts a perspective view of instrument guide 260. Instrument guide 260 may include slots 261, stops 262, and guide piece 264. Slots 261 may allow instrument guide 260 to be coupled to extensions of arms of an inserter. Stops 262 may limit an insertion depth of instrument guide 260 between vertebrae. Stops 262 may have openings 266. Fasteners may be positioned through openings 266 to secure instrument guide 260 to a vertebra during formation of a channel or channels in the vertebra. The fasteners may include, but are not limited to, screws, pins, barbs, or trocars. A head of a fastener may be too large to pass through opening 266.

Guide piece 264 may be used to place a cutting edge of an instrument (e.g., chisel, drill, reamer) at a desired location relative to a vertebra. The instrument may be passed through guide piece opening 268. Guide piece opening may properly orient a cutting portion of the instrument relative to a vertebra that the instrument is to form a channel in. A portion of the instrument may be positioned in groove 270 to guide the cutting edge of the instrument during formation of a channel in the vertebra. As the instrument travels along groove 270, bone matter may be removed from the vertebral surface adjacent to instrument guide 260 to form a groove in the vertebra. Bone matter may be removed to form an opening of a length and/or depth similar to a cross-sectional shape of a coupling projection on an engaging plate.

Figure 37:
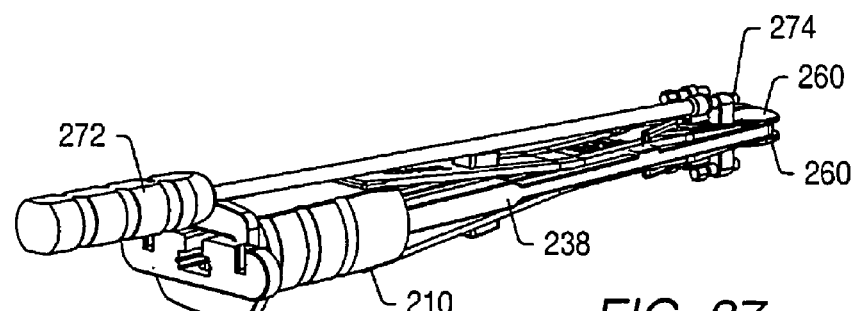
FIG. 37 is a perspective view of an instrument guide coupled to an inserter

FIG. 37 depicts a perspective view of distractor 238, driver 272 and instrument guides 260 coupled to inserter 210. Driver 272 may position a shaft of fastener 274 through an opening in stop 262 so that the fastener couples instrument guide 260 to the vertebra.

Figure 38:
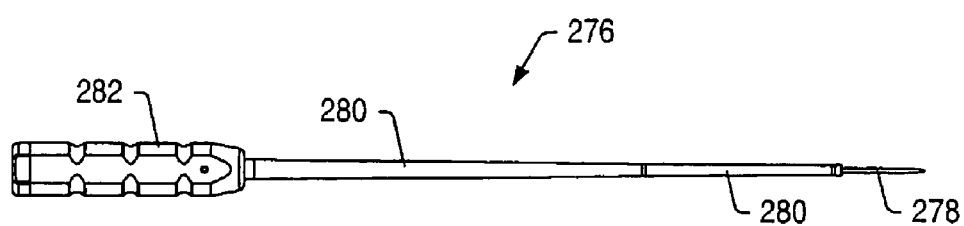
FIG. 38 and FIG. 38A depict an embodiment of a chisel.
Figure 38A:

FIG. 38 depicts a top view of chisel 276. FIG. 38A depicts a side view of chisel 276. Chisel 276 may include end member 278, shaft 280 and handle 282. End member 278 may include a cutting edge capable of penetrating bone. In some embodiments, shaft 280 may be bent to accommodate an angle between a proximal portion of an inserter and a channel guide positioned between vertebrae.

Figure 39:
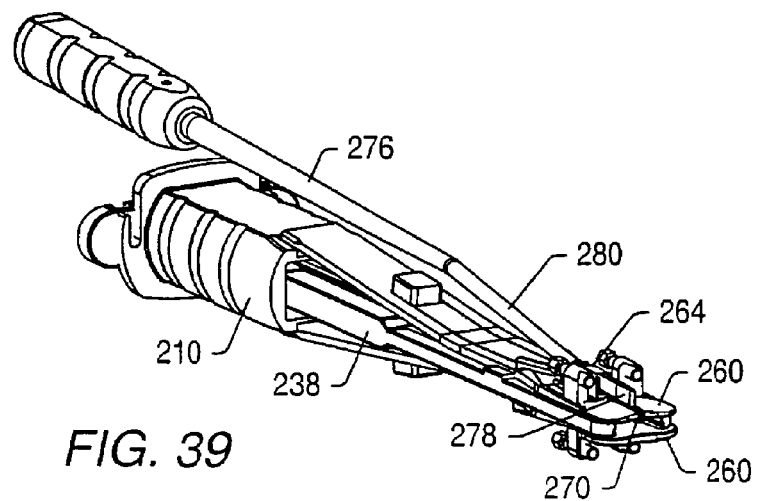
FIG. 39 is a perspective view of a chisel in working relation to an instrument guide.

FIG. 39 depicts a perspective view of instrument guides 260, distractor 238, and chisel 276 coupled to inserter 210. End member 278 of chisel 276 may be inserted through a guide piece opening in guide piece 264 and positioned in groove 270 of instrument guide 260. Cutting edges of end member 278 may be forced into a vertebra. Insertion depth of end member 278 into the vertebra may be monitored using fluoroscopic imaging. In some embodiments, shaft 280 may be marked with a scale. When the end member of the chisel first contacts the vertebra, a first reading of the scale relative to a top of the inserter may be taken. As the chisel is driven into the vertebra, an estimate of the insertion depth may be provided by taking the difference between the current scale reading relative to the top of the inserter and the first reading of the scale relative to the top of the inserter. In some embodiments, a stop may be positioned on shaft 280 to limit insertion depth of the chisel into a vertebra. The stop may contact guide piece 264.

Figure 40:
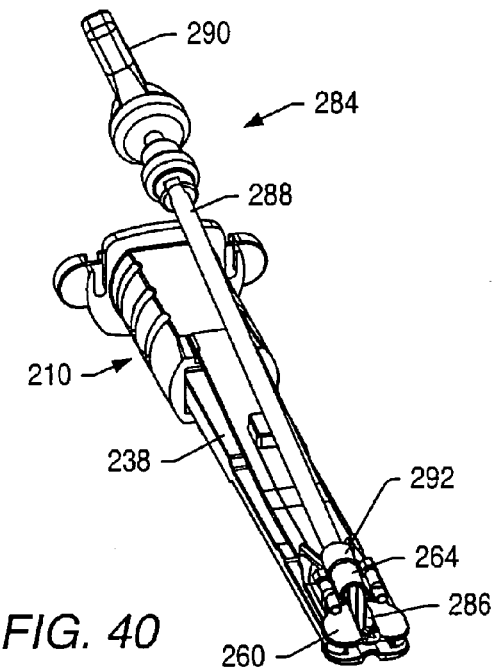
FIG. 40 is a perspective view of a reamer in working relation to an instrument guide.

FIG. 40 depicts a perspective view of a reamer in combination with inserter 210, distractor 238 and instrument guides 260. Reamer 284 may allow removal of bone matter from a vertebral surface to form a groove in the vertebral surface. The groove may have an arcuate cross-sectional shape to complement an arcuate shaped coupling projection on an engaging plate (as shown in FIGS. 9-11). Reamer 284 may include cutter 286, body 288 and handle 290. In some embodiments, a drive shaft may be positioned in body 288. The drive shaft may be coupled to cutter 286 and to handle 290. The drive shaft may be flexible or include flexible joints so that cutter 286 will be oriented in a proper direction relative to the inserter and the vertebra. Cutter 286 may be inserted in an opening of guide piece 264 of instrument guide 260. Rotation of handle 290 may allow cutter 286 to remove vertebral bone and form a groove in the vertebra. Contact of stop 292 with guide piece 264 may limit an insertion depth of cutter 286 into the vertebra. A position of stop 292 along body 288 may be adjustable. In some embodiments, insertion depth of cutter 286 into the vertebra may be monitored during formation of the groove using fluoroscopic imaging.

Figure 41:
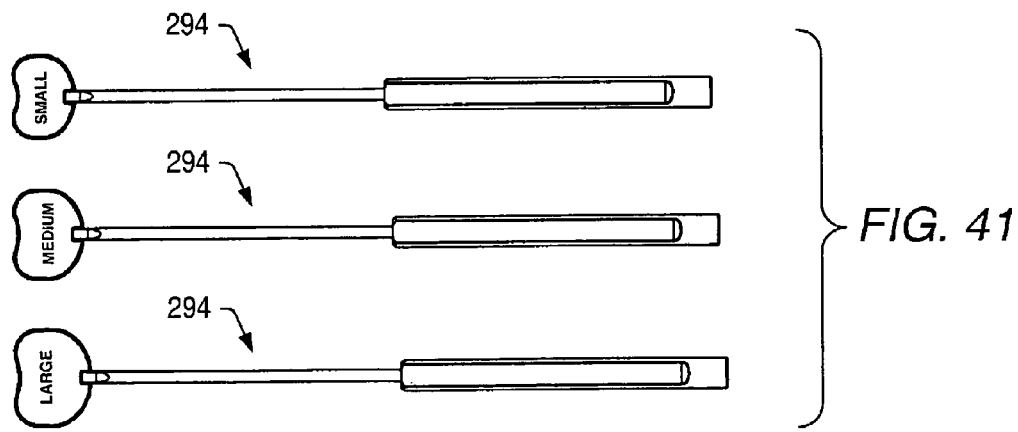
FIG. 41 depicts embodiments of trial spacers.

In certain embodiments, a trial spacer may be used during formation of a disc space between vertebrae. A trial spacer may be used to determine when an appropriate sized disc space is formed between vertebrae. The trial spacer may also determine a size of trial endplates and/or engaging plates. FIG. 41 depicts embodiments of trial spacers 294. A distal end of trial spacer 294 may be similar in size (e.g., small, medium or large) to engaging plates and/or trial endplates.

Figure 42:
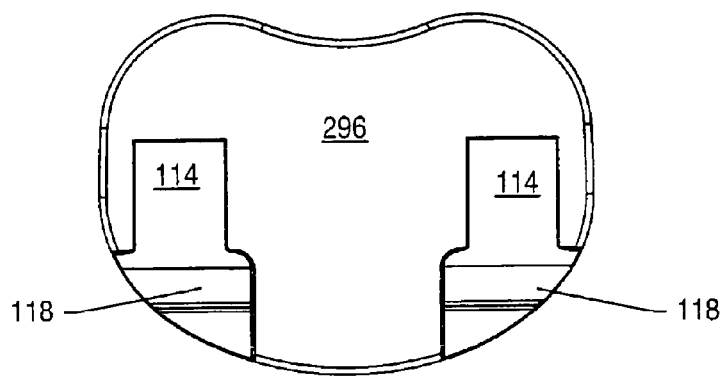
FIG. 42 is a bottom view of an embodiment of a trial endplate.

During some implant insertion procedures, trial endplates may be used to determine the proper height and lordotic angle of the implant to be inserted into the patient. Top surfaces of the trial endplates may be smooth and/or polished so that the trial endplates easily slide between vertebrae. FIG. 42 depicts a bottom view of trial endplate 296. Trial endplate 296 may include slots 114 to engage extensions of arms of an inserter. Slots 114 may include indents 118. Indents 118 may engage detents of an inserter to securely couple the inserter to trial endplate 296.

Trial endplates 296 may vary in thickness. For example, a thickness of trial endplate 296 at an edge near slots 114 may exceed a thickness of the trial endplate at an edge opposite the slots. Trial endplates 296 may have slopes ranging from about 2° to about 22° (e.g., about 3°, about 6°, about 9°, about 12°). The combined angle of a top trial endplate and a bottom trial endplate may determine the lordotic angle that will be established by engaging plates of a implant that correspond to the trial endplates. For example, if two trial endplates with 3° of slope are used, an implant formed between the vertebrae may be formed with two engaging plates, each engaging plate having 3° of slope. The formed implant may establish a 6° lordotic angle between the vertebra. If the top trial endplate has 3° of slope and the bottom trial endplate has 6° of slope, an implant formed between the vertebrae may be formed with a top engaging plate having a 3° slope and a bottom engaging plate having a 6° slope. The formed implant may establish a 9° lordotic angle between the vertebrae.

An instrumentation kit for an implant insertion procedure may include individual trial endplates that correspond in height and slope to each engaging plate supplied in the instrumentation kit. If more than two engaging plates of the same size and slope are supplied in the instrumentation set, only two trial endplates corresponding to that size and slope engaging plate are needed in the instrumentation set. Having a trial endplate that corresponds to each engaging plate allows a surgeon to insert trial endplates that correspond to available engaging plates between the vertebrae. The surgeon is able to test every combination of implant that can be formed using the trial endplates supplied in the instrumentation kit. The surgeon can test an exact model of the implant that is to be formed in the disc space by choosing the appropriate trial endplates and distractor.

When the trial endplates are coupled to an inserter and positioned in the disc space, a distractor may be positioned in the inserter to separate the trial endplates. If the distractor easily slides into the inserter, a larger distractor may be tried. If the distractor cannot be inserted into the inserter, a smaller distractor may be tried. If some force is needed to insert the distractor into the inserter, the distractor may be the appropriate distractor. An appropriate distractor may overdistract vertebrae by about 1.5 mm to about 2.0 mm. Overdistraction of vertebrae by about 1.5 mm to about 2.0 mm may extend ligaments proximate the vertebrae sufficiently to allow for relative movement of components of a disc implant once the implant has been inserted. A fluoroscopic image may be obtained to determine if the trial endplates establish desired lordosis and height between the vertebrae. If the lordosis or height is not correct, other trial endplates and/or distractors may be coupled to the inserter. The inserter may be positioned between the vertebra until the trial endplates and distractor establish a desired height and lordotic angle between the vertebrae. Engaging plates that correspond to the trial endplates and a member that will slide down the distractor may be obtained from the instrumentation kit.

Figure 43:
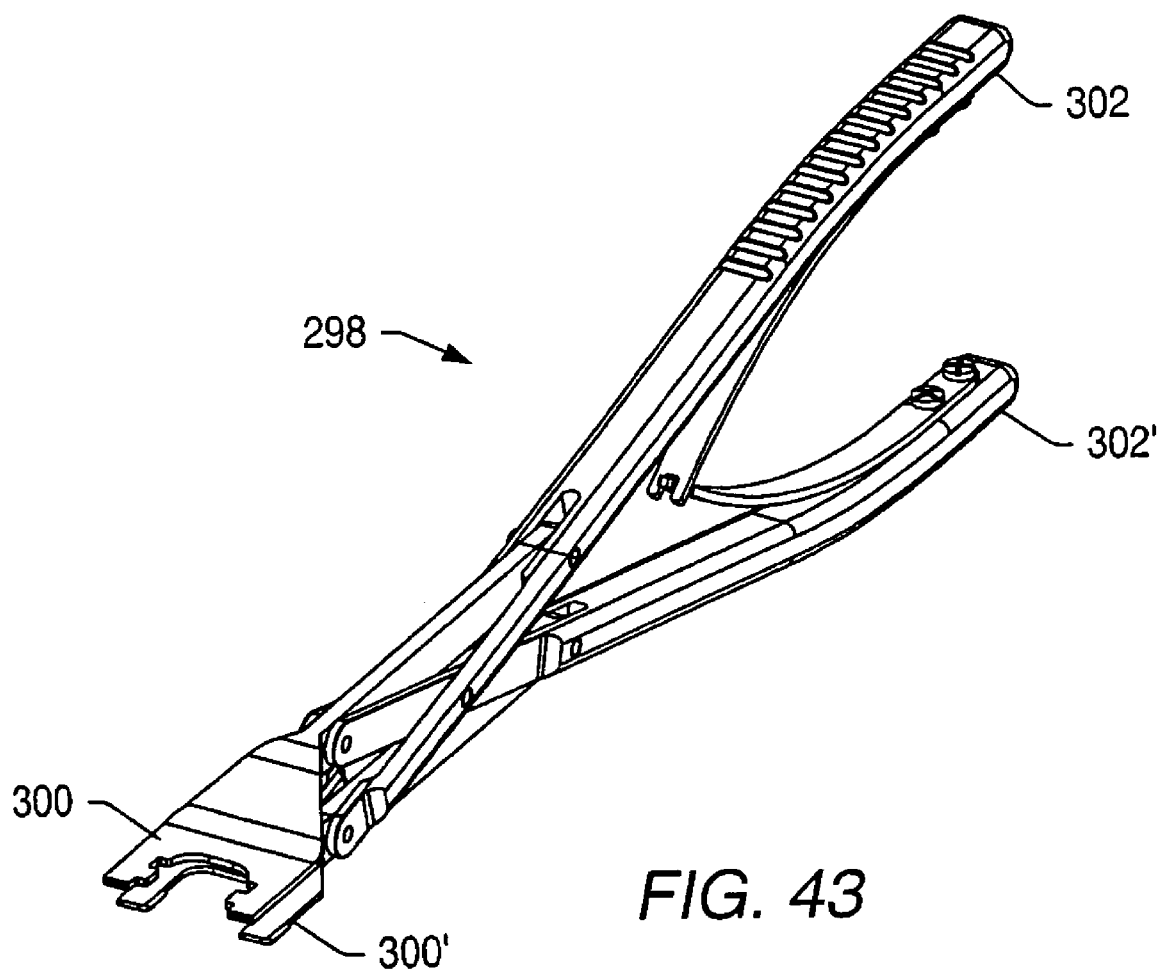
FIG. 43 is a perspective view of a member seater.

FIG. 43 depicts perspective view of a member seater. Member seater 298 may facilitate seating of a member of an implant between engaging plates. Member seater 298 may include arms 300, 300' and handles 302, 302'. Arms 300, 300' may be pivotally coupled to handles 302, 302'. Arm 300' may be positioned on a topside of projection 128 of member 104 (depicted in FIG. 1). Arm 300' may engage slots 114 of engaging plate 102 (depicted in FIG. 1). Compression of handle 302 in the direction of handle 302' may allow arm 300' to move toward arm 300. Movement of arm 300' toward arm 300 may allow member 104 to be securely positioned in recess 116 of engaging plate 102. After seating member 104, member seater 298 may be removed from the intervertebral space.

Engaging plates, members and/or trial endplates may be made of one or more biocompatible materials including, but not limited to, metals, alloys, ceramics, polymers and/or composites. For example, an alloy may include cobalt-chrome-molybdenum (CoCrMo). Ceramics may include, but are not limited to, alumina, zirconia or composites. Polymers used for implant components may include ultra-high molecular weight polyethylene, polyfluorocarbons and/or polyester-esterketone (PEEK). In some embodiments, all components of a disc implant may be formed of metal. In certain embodiments, engaging plates and/or members may be formed of titanium, titanium alloys, steel and/or steel alloys. In addition, materials may be chosen based upon characteristics such as durability and ease with which biological tissue, such as human bone, fuse over with the material. For example, titanium may wear poorly over time, but may fuse well with bone. A cobalt-chrome-molybdenum alloy may wear well, but may not fuse as well with biological tissue.

In some embodiments, engaging plates and/or members may be or may include bioabsorbable material. Surfaces of engaging plates and/or members that contact bone may include a coating to promote osseointegration of the implant component with bone. The coating may be, but is not limited to, a bone morphogenic protein, hydroxyapatite and/or a titanium plasma spray.

In certain embodiments, engaging plates, members and/or trial endplates of an implant may be formed of different materials to decrease wear of the implant over time. An implant embodiment may include engaging plates formed of titanium or cobalt-chrome-molybdenum and one or more members formed of ceramic (such as alumina) or polymer (such as ultra-high molecular weight polyethylene). Material choice may be influenced by various factors. For example, many polymers tend to "flow" when they are produced at less than a certain thickness, possibly deforming and leading to the failure of an implant. Ceramics, however, do not tend to deform, but may potentially shatter under pressure.

In certain embodiments, an implant and/or trial endplates may be distributed and/or sold pre-assembled and stored in sterile packaging until needed. In some implant embodiments, radiological markers may be placed in components of an implant that are invisible to x-rays. The radiological markers may allow the position of the component to be determined using x-rays or other imaging techniques. The ability to determine the position of all components of an implant may eliminate a need to have a surgical procedure to determine the location of the implant.

In some embodiments, steps may be taken to adjust the coefficient of friction of materials used to form engaging plates, members and/or trial endplates. Implant components may be machined, formed and/or chemically treated to decrease the coefficient of friction and reduce the amount of wear on engaging plates and/or members. In some implant embodiments, an insert, coating, liner or other covering may be placed on all, or a portion, of a surface of the engaging plates and/or members. The insert, coating, liner or covering may modify frictional or other physical properties of an engaging plate and/or member relative to another component of an implant. In some embodiments, a surface of a member and/or an inner surface of an engaging plate may include a surface coating to reduce noise resulting from contact between implant components.

An implant may be positioned in an intervertebral space between adjacent vertebrae using an anterior, lateral and/or posterior approach. A surgeon may perform a discectomy to remove all or a portion of an intervertebral disc. Instruments such as curettes, rongeurs and bone shavers may be used to prepare the disc space for the implant. Vertebral surfaces that will contact engaging plates of an implant may be cleaned of cartilage or other tissue. The vertebral surfaces may be shaped to substantially conform to outer surfaces of engaging plates to be placed against the vertebral surfaces.

In an implant insertion procedure, trial spacers may be inserted in the intervertebral space to determine if a formed disc space is sufficiently large and/or to determine a size of an implant to be inserted in the disc space (e.g., small, medium or large). Radiological images may be taken during the discectomy with a trial spacer positioned between the vertebrae to determine if a disc space of the proper width and depth has been formed. One or more marks may be scored or burned into a surface of a vertebra close to a center of an edge of the vertebra. The mark or marks may be used as references to determine a proper lateral position of the implant and/or instrumentation during insertion of the implant.

If needed, instrument guides may be positioned against vertebrae. A reamer or a chisel may be used in conjunction with the instrument guides to form recesses in the vertebrae. The recess may have a shape that conforms to a shape of a coupling projection that extends from an engaging plate of an implant to be positioned between vertebrae.

Trial endplates may be coupled to an inserter. The trial endplates may be positioned between the vertebrae. A distractor of a determined height may be positioned in the inserter to separate the trial endplates. During some insertion procedures, a mallet or other impact device may be used to drive the distractor into the inserter. If the trial endplates and distractor combination do not establish a desired separation height and/or lordotic angle between the vertebrae, different trial endplates and/or different distractors may be tested until a combination of trial endplates and distractor is found that establishes the desired separation height and lordotic alignment of the vertebrae. If removal of trial endplates from a disc space is difficult, a slap hammer or other impact device may be used to facilitate removal of the inserter and trial endplates from the disc space. Using various combinations of trial endplates and distractors may allow a surgeon to determine the correct lordotic angle and height of implant components to be inserted in the intervertebral space.

Engaging plates that correspond to trial spacers that establish a desired separation height and lordotic angle may be chosen from available engaging plates supplied in an instrumentation kit. The chosen engaging plates may be coupled to arms of an inserter. The engaging plates may be positioned in the disc space. The chosen distractor may be positioned in the inserter. During some insertion procedures, a mallet or other impact device may be used to drive the distractor into the inserter. Positioning the distractor in the inserter may separate engaging plates attached to the arms to a desired separation distance. Separation of the engaging plates may force coupling projections of the engaging plates into surfaces of adjacent vertebrae to anchor the engaging plates to the bone.

A member that will slide down channels of the distractor may be obtained from the instrumentation set. The member may be positioned in the distractor and guided between engaging plates with a pusher. The pusher may be coupled to the inserter to maintain a position of the member between the engaging plates. After the member is positioned between the engaging plates, a mechanism on the arms of the inserter may be engaged to release the extension on the arms from the engaging plates. The inserter, distractor and pusher may be removed from the disc space. During some insertion procedures, a slap hammer may be used to facilitate removal of the inserter, distractor and/or pusher from the disc space. Radiological images may be taken to ensure that the implant is positioned as desired.

During some insertion procedures, a member seater may be used after an inserter has been removed from the engaging plates. The member seater may be positioned on a projection of a member and in a slot of an engaging plate. Handles of the member seater may be compressed to securely seat the member in a recess of the engaging plate. The handles may be released to disengage the arms from the projections and from the engaging plate. The member seater may be removed from the intervertebral space.

In this patent, certain U.S. patents have been incorporated by reference. The text of such U.S. patents, is, however, only incorporated by reference to the extent that no conflict exists between such text and the other statements and drawings set forth herein. In the event of such conflict, then any such conflicting text in such incorporated by reference U.S. patents is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A movable disc implant, comprising:
 a first engaging plate for engaging a first surface of a disc space between two vertebral bodies in a spine, wherein said first engaging plate has a first edge, a convex portion, a first inner surface between said first edge and said convex portion, a second edge, a second inner surface between said second edge and said convex portion, and an outer surface, wherein said first inner surface and said second inner surface are sloped relative to said outer surface of said first engaging plate, and wherein said convex portion is a semi-cylindrical portion having a length extending in a first direction parallel to the first edge and an arcuate cross-sectional shape in a plane perpendicular to the first direction;
 a first member having a projection extending in a second direction perpendicular to the first direction, a recess extending along the first direction, a third inner surface and a fourth inner surface, wherein said recess of said first member complements said semi-cylindrical portion of said convex portion of said first engaging plate, wherein said first member and said first engaging plate are positioned such that said convex portion of said first engaging plate at least partially fits in said recess of said first member, said third inner surface of said first member faces said first inner surface of said first engaging plate and said fourth inner surface of said first member faces said second inner surface of said first engaging plate to allow said first member to rock relative to said first engaging plate about an axis parallel to said first direction;

a second member having a recess and a convex portion, wherein said recess of said second member complements said projection of said first member, wherein said convex portion of said second member is a semi-cylindrical portion having a length extending in a third direction perpendicular to the second direction and an arcuate cross-sectional shape in an anteroposterior plane, and wherein said second member has an axis of rotation parallel to the second direction about said projection of said first member, wherein the third direction is perpendicular to the first direction when the implant is in an un-rotated orientation; and a second engaging plate for engaging a second surface of said disc space, wherein said second engaging plate has a recess extending in the third direction having an arcuate cross-sectional shape in an anteroposterior plane that complements said convex portion of said second member.

2. The movable disc implant of claim 1, wherein said second engaging plate further comprises a limiter for limiting anteroposterior movement, lateral movement, or anteroposterior and lateral movement of said first engaging plate, said first member, said second member, and said second engaging plate relative to each other.

3. The movable disc implant of claim 2, wherein said limiter is a projection extending from an inner surface of said second engaging plate.

4. The movable disc implant of claim 2, wherein said limiter is a projection extending along a side of said second engaging plate.

5. The movable disc implant of claim 2, wherein said second member further comprises a surface for contacting said limiter of said second engaging plate, wherein contact between said limiter of said second engaging plate and said surface of said second member limits movement of said second engaging plate relative to said second member.

6. The movable disc implant of claim 5, wherein said surface of said second member is sloped.

7. The movable disc implant of claim 1, wherein a first thickness of said first engaging plate proximate said convex portion exceeds a second thickness proximate said first and said second edges.

8. The movable disc implant of claim 1, wherein said first member has a first edge and a second edge, and wherein a first thickness of said first member proximate said recess exceeds a second thickness of said first member proximate said first and second edges of said first member.

9. The movable disc implant of claim 1, wherein a range of said rotation of said second member relative to said first member is limited by a size or shape of said recess of said second member relative to a complementary size or shape of said projection of said first member.

10. The movable disc implant of claim 1, wherein said projection of said first member is located near a center of said movable disc implant.

11. The movable disc implant of claim 1, wherein said projection of said first member is located off-center of said movable disc implant.

12. The movable disc implant of claim 1, wherein said projection of said first member has a flat surface.

13. The movable disc implant of claim 1, wherein said first engaging plate has a coupling projection.

14. The movable disc implant of claim 1, wherein said second engaging plate has a coupling projection.

15. The movable disk implant of claim 1 wherein the semi-cylindrical portion of said convex portion of said first engaging plate the semi-cylindrical portion has a constant arcuate cross-sectional area and wherein the length of the semi-cylindrical portion extends from proximate to a third edge of the first engaging plate to proximate to a fourth edge of the first engaging plate, wherein the third and fourth edges are perpendicular to the first and second edges of the first engaging plate.

16. A movable disc implant, comprising:

a first engaging plate for engaging a first surface of a disc space between two vertebral bodies in a spine, wherein said first engaging plate has a projection extending from an inner surface of the first engaging plate and an opening defined in the inner surface of the first engaging plate;

a first member having a recess, a convex portion that is a semi-cylindrical portion with arcuate cross-section and a length extending in a direction, and one or more stops extending radially from the ends of the convex portion, wherein said recess of said first member complements said projection of said first engaging plate;

a coupler extending through at least a portion of said first member into said opening of said first engaging plate;

a second member having a recess and a convex portion, wherein said recess of said second member complements said convex portion of said first member, wherein said convex portion of said second member is a semi-cylindrical shape with an arcuate cross-sectional shape and a length extending in a second direction perpendicular to the anteroposterior direction, and wherein said one or more stops of said first member restrict anteroposterior translation of said second member relative to said first member; and a second engaging plate for engaging a second surface of said disc space, wherein said second engaging plate has a recess having an arcuate cross-sectional shape that complements said convex portion of said second member.

17. The movable disc implant of claim 16, wherein said opening of said first engaging plate extends through said first engaging plate.

18. The movable disc implant of claim 16, wherein said opening of said first engaging plate extends to a fixed depth in said first engaging plate such that the opening is only open to the inner surface of the first engaging plate.

19. The movable disc implant of claim 16, wherein said first engaging plate further comprises a first end, a first inner surface extending from said first end, a second end, a second inner surface extending from said second end, and an outer surface, and wherein said first inner surface and said second inner surface are sloped relative to said outer surface of said first engaging plate.

20. The movable disc implant of claim 16, wherein said coupler comprises a head and shank, wherein the head is wider than the shank, wherein said first member has an opening aligned with the opening of said first engaging plate, and wherein said head of said coupler is recessed in said opening of said first member and said shank is received in the opening of said first engaging plate.

* * * * *